(12) United States Patent
Yuan et al.

(10) Patent No.: US 6,413,982 B1
(45) Date of Patent: Jul. 2, 2002

(54) 4-SUBSTITUTED QUINOLINE DERIVATIVES

(75) Inventors: Jun Yuan, Guilford; George D. Maynard, Clinton; Alan Hutchison, Madison; Stanislaw Rachwal, Branford, all of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/536,922

(22) Filed: Mar. 28, 2000

Related U.S. Application Data

(60) Provisional application No. 60/126,926, filed on Mar. 29, 1999.

(51) Int. Cl.$^7$ .................... A61L 31/47; C07D 215/16; C07D 215/38
(52) U.S. Cl. .................... 514/314; 514/312; 514/313; 546/153; 546/159; 546/167
(58) Field of Search .................... 514/314, 312, 514/313; 546/167, 154, 153

(56) References Cited

U.S. PATENT DOCUMENTS

| | | | |
|---|---|---|---|
| 5,792,766 A | | 8/1998 | Chen et al. |
| 6,228,868 B1 | * | 5/2001 | Gwaltney |

FOREIGN PATENT DOCUMENTS

| | | |
|---|---|---|
| WO | WO 95/11885 A | 5/1995 |
| WO | WO 95/32948 | 12/1995 |
| WO | WO 96/02509 A1 | 2/1996 |
| WO | WO 96/20193 | 7/1996 |
| WO | WO 97/19926 | 6/1997 |
| WO | WO 97/19927 | 6/1997 |
| WO | WO 97/19928 | 6/1997 |
| WO | WO 97/21680 | 7/1997 |
| WO | WO 98/52942 A1 | 11/1998 |
| WO | WO 99/14196 | 3/1999 |

OTHER PUBLICATIONS

CA 121:255787, Hatano, 1994.*
Lakhani, CA 109:149419, 1988.*
Lakhani, CA 117:48192, 1991.*
Vostrova, CA 91:193127, 1979.*
Giardina et al., (1997) "Discovery of a Novel Class of Selective Non–Peptide Antagonists for the Human Neurokinin–3 Receptor. 1. Identification of The 4–Quinolinecarboxamide Framework", *Journal of Medicinal Chemistry*, vol. 40, pp. 1794–1807.
Raveglia et al., (1997) "A Nobel Synthesis of 3–Halo–2–phenylquinoline–4–carboxylic Acids", *J. Heterocyclic Chem.* vol. 34 pp. 557–559.
Giardina et al., (1998) "Discovery of a Novel Class of Selective Non–Peptide Antagonists for the Human Neurokinin–3 Receptor. 2. Identification of (S)–N–(1–Phenylpropyl)–3–hydroxy–2–phenylquinoline–4–carboxamide (SB 223412)", *Journal of Medicinal Chemistry*.
Sarau et al., (1997) "Nonpeptide Tachykinin receptor Antagonists: I. Pharmacological and Pharmacokinetic Characterization of SB 223412, a Novel, Potent and Selective Neurkinin–3 Receptor Antagonist", *The Journal of pharmacology and Experimental Therapeutics*, vol. 281, No. 3, pp. 1303–1311.
Giardina et al., (1997) "Lead generation and lead optimization processes in the discovery of selective nonpeptide neurokinin receptor antagonists" *Drugs of the Future*, vol. 22, No. 11, 1235–1257.
Giardinia et al. (1999) "Replacement of the quinoline system in 2–phenyl–4–quinolincarboxamide NK–3 receptor antagonists", *IL Farmaco*, vol. 54, pp. 364–374.
Raveglia et al., "Quinoline NK–3 Receptor Antagonists: Chemical Strategies to Prevent (æ–1) Metabolic Oxidation", pp. 62, 1982.
Giardina et al., "2–Pheny–4–quinolinecarboxamides: A Novel Class of Potent and Selective Non–Peptide Competitive Antagonists for the Human Neurokinin–3 Receptor", *Journal of Medicinal Chemistry*, vol. 39, No. 12, pp. 2281–2284, 1993.
Piero Savarino et al., "Assembled systems (X–azolopyridine)(quinoline). Bases and Salts.", *Journal of Heterocyclic Chemistry*, vol. 29, 1992, pp. 185–192, XP002144891.
Giardina et al., "Reliable And Efficient Synthesis of SR 142801", Bioorg. Med. Chem. Lett., 6(19), (1996), 2307–2310.

* cited by examiner

*Primary Examiner*—D. Margaret Seaman
(74) *Attorney, Agent, or Firm*—McDonnell Boehnen Hulbert & Berghoff

(57) ABSTRACT

Disclosed are compounds of the Formula where $R_1$, $R_2$, $R_3$, $R_4$, X, $Y_1$, and $Y_2$ are defined herein. These compounds bind with high affinity to NK-3 receptors and/or $GABA_A$ receptors. Also provided are pharmaceutical compositions comprising these compounds, and methods of treating patients suffering from various central nervous system and peripheral diseases or disorders with these pharmaceutical compositions. This invention also relates to the use of such compounds in combination with one or more other CNS agents to potentiate the effects of the other CNS agents. The compounds of this invention are also useful as probes for the localization of NK-3 receptors and $GABA_A$ receptors.

52 Claims, No Drawings

4-SUBSTITUTED QUINOLINE DERIVATIVES

This application claims benefit of U.S. provisional application serial No. 60/126,926, filed Mar. 29, 1999.

BACKGROUND OF THE INVENTION

1. Field of the Invention

This invention relates to quinoline derivatives, pharmaceutical compositions comprising them, and the use of such compounds in the treatment of central nervous system and peripheral diseases or disorders. This invention also relates to the use of such compounds in combination with one or more other CNS agents to potentiate the effects of the other CNS agents. The compounds of this invention are also useful as probes for the localization of cell surface receptors.

2. Description of the Related Art

The tachykinins represent a family of structurally related peptides originally isolated based upon their smooth muscle contractile and sialogogic activity. These mammalian peptides include substance P (SP), neurokinin A (NKA) and neurokinin β (NKB). Tachykinins are synthesized in the central nervous system (CNS), as well as in peripheral tissues, where they exert a variety of biological activities. Substance P can be produced from three different mRNAs (α-, β- and γ-preprotachykinin mRNAs) that arise from a single gene as a result of alternative RNA splicing, whereas NKA can be generated from either the β- or the γ-preprotachykinin MRNA through posttranslationally processed precursor polypeptides. These precursors can also be differentially processed so that amino terminally extended forms of NKA (known as neuropeptide K and neuropeptide γ) are produced. NKB is produced from a separate mRNA arising from a second gene known as preprotachykinin B.

Three receptors for the tachykinin peptides have been molecularly characterized and are referred to as neurokinin-1 (NK-1), neurokinin-2 (NK-2) and neurokinin-3 (NK-3) receptors. The NK-1 receptor has a natural agonist potency profile of SP>NKA>NKB. The NK-2 receptor agonist potency profile is NKA>NKB>SP, and the NK-3 receptor agonist potency profile is NKB>NKA>SP. These receptors mediate the variety of tachykinin-stimulated biological effects that generally include 1) modulation of smooth muscle contractile activity, 2) transmission of (generally) excitatory neuronal signals in the CNS and periphery (e.g. pain signals), 3) modulation of immune and inflammatory responses, 4) induction of hypotensive effects via dilation of the peripheral vasculature, and 5) stimulation of endocrine and exocrine gland secretions. These receptors transduce intracellular signals via the activation of pertussis toxin-insensitive ($G_{\alpha q/11}$) G proteins, resulting in the generation of the intracellular second messengers inositol 1,4,5-trisphosyphate and diacylglycerol. NK-1 receptors are expressed in a wide variety of peripheral tissues and in the CNS. NK-2 receptors are expressed primarily in the periphery, while NK-3 receptors are primarily (but not exclusively) expressed in the CNS. Recent work confirms the presence of NK-3 receptor binding sites in the human brain.

Studies measuring the localization of NKB and NK-3 receptor mRNAs and proteins, along with studies performed using peptide agonists and non-peptide NK-3 receptor antagonists, provide a rationale for using NK-3 receptor antagonists in treating a variety of disorders in both the CNS and the periphery. In the CNS, activation of NK-3 receptors has been shown to modulate dopamine and serotonin release, indicating therapeutic utility in the treatment of a variety of disorders including anxiety, depression, schizophrenia and obesity. Further, studies in primate brain detect the presence of NK-3 MRNA in a variety of regions relevant to these disorders. With regard to obesity, it has also been shown that NK-3 receptors are located on MCH-containing neurons in the rat lateral hypothalamus and zona incerta. In the periphery, administration of NKB into the airways is known to induce mucus secretion and bronchoconstriction, indicating therapeutic utility for NK-3 receptor antagonists in the treatment of patients suffering from airway diseases such as asthma and chronic obstructive pulmonary disease (COPD). Localization of NK-3 receptors in the gastrointestinal (GI) tract and the bladder indicates therapeutic utility for NK-3 receptor antagonists in the treatment of GI and bladder disorders including inflammatory bowel disease and urinary incontinence.

Both peptide and nonpeptide antagonists have been developed for each of the tachykinin receptors. The first generation of peptide antagonists for the tachykinin receptors had problems with low potency, partial agonism, poor metabolic stability and toxicity, whereas the current generation of non-peptide antagonists display more drug-like properties. Unfortunately, previous non-peptide NK-3 receptor antagonists suffer from a number of problems such as species selectivity (which limits the potential to evaluate these compounds in many appropriate disease models). New non-peptide NK-3 receptor antagonists are therefore being sought, both as therapeutic agents and as tools to further investigate the anatomical and ultrastructural distribution of NK-3 receptors, as well as the physiologic and pathophysiologic consequences of NK-3 receptor activation.

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$, (Mohler et. al. *Neuroch. Res.* 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of various other CNS active compounds. For example, there is evidence that selective serotonin reuptake inhibitors (SSRIs) may show greater antidepressant activity when when used in combination with $GABA_A$ selective ligands than when used alone.

SUMMARY OF THE INVENTION

Disclosed are compounds, particulary quinoline derivatives that bind to cell surface receptors. Preferred compounds of the invention bind to neurokinin and/or GABA receptors, in particular these compounds possess affinity for NK-3 receptors and/or $GABA_A$ receptors. These compounds are therefore considered to be of potential use in the treatment of a broad array of diseases or disorders in patients which are characterized by modulation of NK-3 and/or $GABA_A$ receptors.

This invention provides compounds of general Formula I:

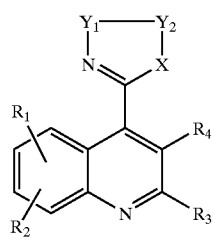

Formula I or pharmaceutically acceptable salts or pharmaceutically acceptable solvates thereof, wherein in $R_1$, $R_2$, $R_3$, $R_4$, X, $Y_1$ and $Y_2$ are hereinafter defined.

Preferred compounds of this invention are ligands for neurokinin receptors and GABA receptors, especially NK-3 receptors and $GABA_A$ receptors, and are useful in the treatment of a wide range of diseases or disorders including, but not limited to depression, anxiety, sleep disorders, cognitive disorders, low alertness, psychosis, obesity, pain, Parkinson's disease, Alzheimer's disease, neurodegenerative diseases, movement disorders, Down's syndrome, benzodiazepine overdoses, respiratory diseases, inflammatory diseases, neuropathy, immune disorders, migraine, biliary disfunction, and dermatitis.

The invention also provides pharmaceutical compositions comprising compounds of Formula I. The invention further comprises a method of treating a patient suffering from various central nervous system and peripheral diseases or disorders with an effective amount of a compound of the invention. Treatment of humans, domesticated companion animals (pets) or livestock animals suffering such conditions with an effective amount of a compound of the invention is contemplated by the invention.

Packaged pharmaceutical compositions including instructions for use of the composition are also included.

In a separate aspect, the invention provides a method of potentiating the actions of other CNS active compounds. This method comprises administering an effective amount of a compound of the invention with another CNS active compound.

The invention furthermore provides methods of using compounds of this invention as positive controls in assays for receptor activity and using appropriately labeled compounds of the invention as probes for the localization of receptors, particularly NK-3 and/or $GABA_A$ receptors, in tissue sections.

DETAILED DESCRIPTION OF THE INVENTION

This invention relates to quinoline derivatives, pharmaceutical compositions comprising them, and the use of such compounds in the treatment of various central nervous system and peripheral diseases or disorders.

Accordingly, a broad embodiment of the invention is directed to compounds of Formula I:

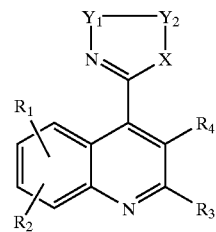

Formula I or pharmaceutically acceptable salts or pharmaceutically acceptable solvates thereof, wherein:

$R_1$ is selected from:
hydrogen, halogen, hydroxy, $C_{1-6}$ alkyl, —O($C_{1-6}$ alkyl), —$NO_2$, —CN, —$SO_2NH_2$, —$SO_2NH(C_{1-6}$ alkyl), —$SO_2N$ ($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$ ($C_{1-6}$ alkyl), —NHSO$_2$($C_{1-6}$ alkyl), —N($C_{1-6}$ alkyl) $SO_2$($C_{1-6}$ alkyl), —$SO_2$NHCO($C_{1-6}$ alkyl), —CONHSO$_2$($C_{1-6}$ alkyl), —CON($C_{1-6}$ alkyl)($C_{1-6}$ alkyl), —$CO_2$($C_{1-6}$ alkyl), —S($C_{1-6}$ alkyl), —SO ($C_{1-6}$ alkyl), or —$SO_2$($C_{1-6}$ alkyl),
wherein said $C_{1-6}$ alkyl may be straight, branched or cyclic, may contain one or two double or triple bonds, unsubstituted or substituted with one or more substituents selected from: hydroxy, oxo, fluoro, amino, $C_{1-3}$ alkoxy;

$R_2$ and $R_3$ are independently selected from the groups consisting of:
(1) $C_{1-8}$ alkyl, wherein said $C_{1-8}$ alkyl is be straight, branched or cyclic, may contain one or two double or triple bonds, and is unsubstituted or substituted with one or more of the substituents selected from:
(i) hydroxy, (ii) oxo,
(iii) fluoro,
(iv) amino,
(v) $Ar_1$, wherein $Ar_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from:

hydrogen, halogen, hydroxy, $C_{1-6}$ alkyl, —O($C_{1-6}$ alkyl), —$NO_2$, —CN, —$SO_2NH_2$, —$SO_2NH(C_{1-6}$ alkyl), —$SO_2N(C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —$NHSO_2$($C_{1-6}$ alkyl), —N($C_{1-6}$ alkyl)$SO_2$($C_{1-6}$ alkyl), —$SO_2$NHCO($C_{1-6}$ alkyl), —$CONHSO_2$($C_{1-6}$ alkyl), —CON($C_{1-6}$ alkyl)($C_{1-6}$ alkyl), —$CO_2$($C_{1-6}$ alkyl), —S($C_{1-6}$ alkyl), —SO($C_{1-6}$ alkyl), or —$SO_2$($C_{1-6}$ alkyl), wherein $C_{1-6}$ alkyl, is defined as above, (vi) —$NR_5R_6$, wherein $R_5$ and $R_6$ are independently selected at each occurrence from:
(a) hydrogen,
(b) $C_{1-6}$ alkyl, wherein $C_{1-6}$ alkyl is as defined above,
(c) —$(CH_2)n$—$Ar_1$, wherein n is 0, 1 or 2, and $Ar_1$ is as defined above, or the groups $R_5$ and $R_6$ may be joined together to form a 4- to 8-membered ring of which the 4- to 8-membered ring may contain one or two double bonds, or one or two oxo, or one or two O, S or N—$R_7$ wherein $R_7$ is independently selected at each occurrence from hydrogen, $C_{1-6}$ alkyl, —$(CH_2)n$-$Ar_1$, wherein $C_{1-6}$ alkyl, n and $Ar_1$ are defined as above, (vii) —$OR_5$, wherein $R_5$ is as defined above,
(viii) —$CONR_5R_6$ wherein $R_5$ and $R_6$ are as defined above,
(ix) —$CO_2R_5$, wherein said $R_5$ is as defined above;

(2) $Ar_2$, wherein $Ar_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:

hydrogen, halogen, hydroxy, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2$NHCO($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl), or —$SO_2$($C_{1-8}$ alkyl), wherein said $C_{1-8}$ alkyl is as defined above;

(3) —$NR_8R_9$, wherein $R_8$ and $R_9$ are independently selected at each occurrence from:
(a) hydrogen,
(b) $Ar_2$, wherein $Ar_2$ is as defined above;
(c) $C_{1-8}$ alkyl, wherein said $C_{1-8}$ alkyl is as defined above;

or the groups $R_8$ and $R_9$ may be joined together to form a 4- to 8-membered ring of which the 4- to 8-membered ring may contain one or more double bonds; one or more oxo; one or more O, S(O)n, N—$R_7$ wherein n and $R_7$ are as defined above; one or more groups consisting of hydroxy, halogen, amino, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2$NHCO($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl), or —$SO_2$ ($C_{1-8}$ alkyl), wherein said $C_{1-8}$ alkyl is as defined above;

(4) —$OR_8$, wherein $R_8$ is as defined above;

$R_4$ is selected from:
hydrogen, halogen, hydroxy, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2$NHCO($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO ($C_{1-8}$ alkyl), —$SO_2$($C_{1-8}$ alkyl), or $Ar_2$ wherein $Ar_2$ and said $C_{1-8}$ alkyl are as defined above;

X is NH, O or N—$R_{10}$, wherein $R_{10}$, is $C_{1-8}$ alkyl, wherein said $C_{1-8}$ alkyl is defined as above;

$Y_1$ is —$CR_{11}R_{12}$—, —$CR_{11}R_{12}(CH_2)_p$—, —$(CH_2)_p$ $CR_{11}R_{12}$—, or —$(CH_2)_pCO$—; where p is 0, 1, or 2; and $R_{11}$ and $R_{12}$ are independently selected at each occurrence from:
(1) hydrogen,
(2) $Ar_2$, wherein $Ar_2$ is as defined above;
(3) $C_{1-8}$ alkyl wherein $C_{1-8}$ alkyl is as defined above;
(4) —$CONR_8R_9$ wherein $R_8$ and $R_9$ are as defined above,
(5) —$CO_2R_8$, wherein said $R_8$ is as defined above; or the groups $R_{11}$ and $R_{12}$ may be joined together to form a monocyclic, bicyclic, or tricyclic ring;

$Y_2$ is —$CR_{11}R_{12}$— or —CO— with the proviso that $Y_2$ is not —CO— when $Y_1$ is —$(CH_2)_pCO$—, wherein p, $R_{11}$ and $R_{12}$ are as defined above; and when X is N—$R_{10}$, the groups $R_{10}$ and $R_{11}$ may be joined to form a 5- to 8-membered ring which may contain one or more double bonds; one or more oxo; one or more O, S(O)n, N—$R_7$ wherein n and $R_7$ are as defined above; one or more groups consisting of hydroxy, halogen, amino, $C_{1-8}$ alkyl, —O($C_{1-8}$ alkyl), —$NO_2$, —CN, —$SO_2NH_2$, —$SO_2NH(C_{1-8}$ alkyl), $SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2$NHCO ($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl), or —$SO_2$($C_{1-8}$ alkyl) wherein said $C_{1-8}$ alkyl is as defined above.

Preferred compounds include compounds of Formula I, and the pharmaceutically acceptable salts and solvates thereof, wherein X is NH or N—$R_{10}$, where $R_{10}$ is as defined as for Formula I.

Other preferred compounds of general Formula I include compounds of Formula IA

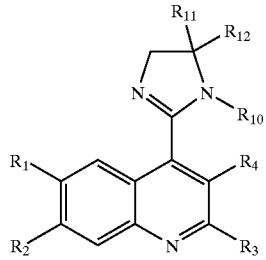

Formula IA and the pharmaceutically acceptable salts and solvates thereof, wherein: $R_1$, $R_2$, $R_3$, $R_4$, $R_{10}$, $R_{11}$, and $R_{12}$ are as defined as for Formula I.

More preferred compounds of general Formula I include compounds of Formula IB

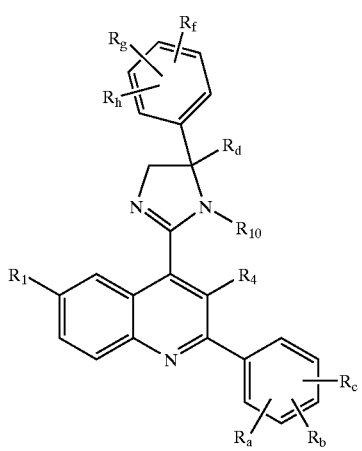

Formula IB and the pharmaceutically acceptable salts and solvates thereof, wherein: $R_1$ and $R_4$ are as defined in Formula I;

$R_a$, $R_b$, and $R_c$ and $R_f$, $R_g$, and $R_h$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO ($C_{1-6}$ alkyl), —N($C_{1-6}$ alkyl)$CO_2$($C_{1-6}$ alkyl), —CON ($C_{1-6}$ alkyl)($C_{1-6}$ alkyl), —$CO_2$($C_{1-6}$ alkyl);

$R_d$ is hydrogen, straight or branched chain alkyl, or straight or branched chain alkoxy; and $R_{10}$ is hydrogen, methyl or ethyl.

Additional preferred compounds of general Formula I are compounds of Formula IC

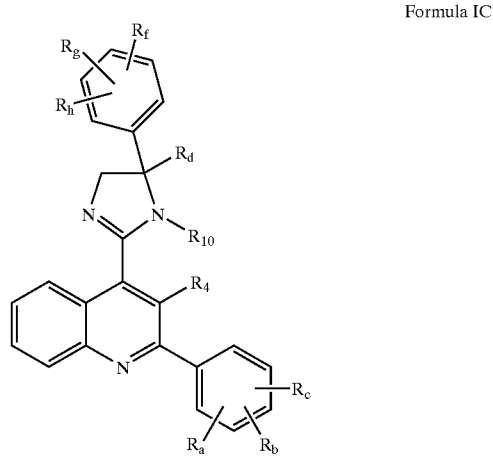

Formula IC and the pharmaceutically acceptable salts and solvates thereof, wherein:

$R_1$ and $R_4$ are as defined in Formula I;

$R_a$, $R_b$, and $R_c$ and $R_f$, $R_g$, and $R_h$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO ($C_{1-6}$ alkyl), —N($C_{1-6}$ alkyl)$CO_2$($C_{1-6}$ alkyl), —CON ($C_{1-6}$ alkyl)($C_{1-6}$ alkyl), —$CO_2$($C_{1-6}$ alkyl);

$R_d$ is hydrogen or straight or branched chain alkyl or straight or branched chain alkoxy;

$R_4$ is as defined in Formula I and $R_{10}$ is hydrogen, methyl or ethyl.

Still other preferred compounds of general Formula I include compounds of Formula ID

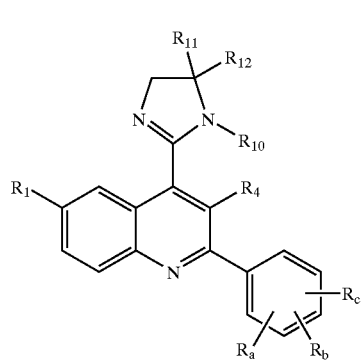

Formula ID and the pharmaceutically acceptable salts and solvates thereof, wherein:

$R_a$, $R_b$, and $R_c$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —CON($C_{1-6}$ alkyl)($C_{1-6}$ alkyl), —CO$_2$($C_{1-6}$ alkyl), wherein $C_{1-6}$alkyl is as defined above;

$R_4$ is as defined for Formula I;

$R_{10}$ is hydrogen, methyl or ethyl; and $R_{11}$ and $R_{12}$ are joined together to form a monocyclic, bicyclic, or tricyclic ring.

Yet other preferred compounds of general Formula I include compounds of Formula IE

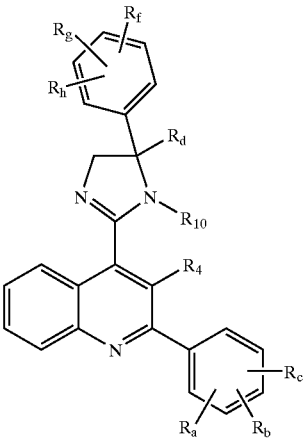

Formula IE and the pharmaceutically acceptable salts and solvates thereof, wherein:

$R_a$, $R_b$, and $R_c$ and $R_f$, $R_g$, and $R_h$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO ($C_{1-6}$ alkyl), —N($C_{1-6}$ alkyl)CO$_2$($C_{1-6}$ alkyl), —CON ($C_{1-6}$ alkyl)($C_{1-6}$ alkyl), —CO$_2$($C_{1-6}$ alkyl);

$R_4$ is as defined for Formula I; and $R_d$ and $R_{10}$ together form an alkylene group of from 3–5 carbon atoms each of which is optionally substituted with methyl or ethyl.

Another class of preferred compounds of general Formula I includes compounds of Formula IF

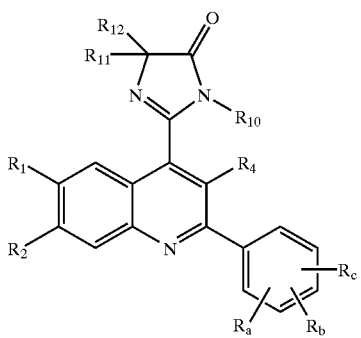

Formula IF and the pharmaceutically acceptable salts and solvates thereof, wherein:

$R_a$, $R_b$, and $R_c$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —CON($C_{1-6}$ alkyl) ($C_{1-6}$ alkyl), —CO$_2$($C_{1-6}$ alkyl), wherein $C_{1-6}$alkyl is as defined above;

$R_1$, $R_2$, and $R_4$ are as defined in Claim 1;

$R_{10}$ is hydrogen, methyl or ethyl; and $R_{11}$ and $R_{12}$ are independently from:

(1) hydrogen, (2) Ar$_2$, (3) —$C_{1-8}$ alkyl, (4) —CONR$_8$R$_9$ wherein $R_8$ and $R_9$ are as defined in Claim 1, and (5) —CO$_2$R$_8$, wherein said $R_8$ is as defined in Claim 1.

Particularly preferred compounds of Formula IF are compounds of Formula IG

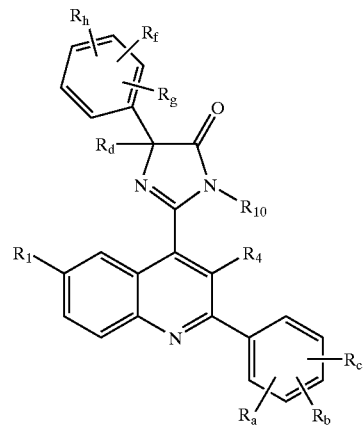

Formula IG and the pharmaceutically acceptable salts and solvates thereof, wherein:

$R_a$, $R_b$, and $R_c$ and $R_f$, $R_g$, and $R_h$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO ($C_{1-6}$ alkyl), —N($C_{1-6}$ alkyl)CO$_2$($C_{1-6}$ alkyl), —CON ($C_{1-6}$ alkyl)($C_{1-6}$ alkyl), —CO$_2$($C_{1-6}$ alkyl);

$R_d$ is hydrogen or straight or branched chain alkyl or straight or branched chain alkoxy;

$R_1$ and $R_4$ are as defined for Formula I; and $R_{10}$ is hydrogen, methyl or ethyl.

Also, preferred compounds of the invention include compounds of general Formula IA wherein X is oxygen. These compounds will be referred to as compounds of Formula IH.

More preferred compounds of Formula IH are compounds of Formula Ii

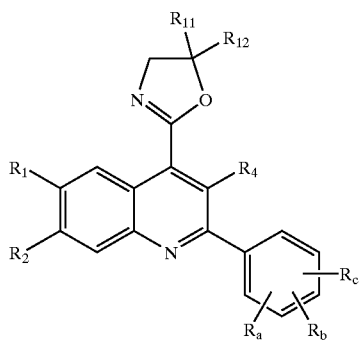

Formula Ii and the pharmaceutically acceptable salts and solvates thereof, wherein:

$R_1$, $R_2$, $R_4$, $R_{11}$, and $R_{12}$ are as defined for Formula I; and $R_a$, $R_b$, and $R_c$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —CON($C_{1-6}$alkyl)($C_{1-6}$ alkyl), —CO$_2$($C_{1-6}$ alkyl).

Particularly preferred compounds of Formula IH are compounds of Formula IJ

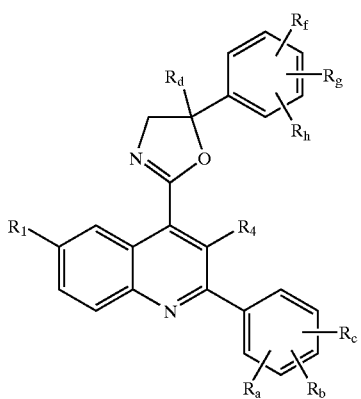

Formula IJ and the pharmaceutically acceptable salts and solvates thereof, wherein:

$R_1$ and $R_4$ are as defined for Formula I;

$R_a$, $R_b$, and $R_c$ and $R_f$, $R_g$, and $R_h$ independently represent hydrogen, halogen, hydroxy, $C_{1-6}$ alkyl, —O($C_{1-6}$ alkyl), —NO$_2$, —CN, —SO$_2$NH$_2$, amino, —NH($C_{1-6}$ alkyl), —N($C_{1-6}$ alkyl)($C_{1-6}$ alkyl), —N($C_{1-6}$ alkyl)CO ($C_{1-6}$ alkyl), —N($C_{1-6}$ alkyl)CO$_2$($C_{1-6}$ alkyl), —CON ($C_{1-6}$ alkyl)($C_{1-6}$ alkyl), —CO$_2$($C_{1-6}$ alkyl); and $R_d$ is hydrogen or straight or branched chain alkyl or straight or branched chain alkoxy.

In certain instances, the compounds of the present invention have asymmetric centers and this invention includes all of the optical isomers and mixtures thereof.

In addition compounds with carbon-carbon double bonds may occur in Z— and E— forms with all isomeric forms of the compounds being included in the present invention.

When any variable (e.g. alkyl, $Ar_1$, $Ar_2$, $R_5$, $R_6$, $R_8$, $R_9$, $R_{11}$, $R_{12}$, etc.) occurs more than one time in Formula I, its definition on each occurrence is independent of its definition at every other occurrence.

As used herein, the term "alkyl" includes straight or branched chain alkyl groups and cycloalkyl groups that also may contain double or triple bonds. Examples of "alkyl" include methyl, ethyl, propyl, isopropyl, butyl, iso-, sec- and tert-butyl, pentyl, hexyl, heptyl, 3-ethylbutyl, cyclopropyl, cyclobutyl, cyclopentyl, cyclohexyl, cycloheptyl, norbornyl, and the like. Where the number of carbon atoms is designed at the alkyl group includes that number of carbon atoms. When reference is made herein to $C_{1-6}$ alkyl which it may contain one or two double or triple bond it is understood that at least two carbons are present in the alkyl for one double or triple bond, and at least four carbons for two double or triple bonds. The term "alkoxy" represents an alkyl group of indicated number of carbon atoms attached through an oxygen bridge, such as methoxy, ethoxy, propoxy and iso-propoxy.

By the term "halogen" is meant fluorine, chlorine, bromine, and iodine.

The term "monocyclic" includes, but is not limited to cyclopentyl, cyclohexyl or cycloheptyl; "bicyclic" includes, but is not limited to indanyl, tetrahydronaphthyl, chromanyl benzo[a][7]annulenyl, bicyclo[4.4.0]decanyl, bicyclo[4,3.0] nonanyl, bicyclo[3.3.0]octanyl; "tricyclic" includes, but is not limited to dibenzoannulenyl, dibenzoxepanyl, dibezothi-epanyl.

As used herein, the terms "patients" refers to humans as well as other mammals including pets such as dogs and cats and livestock such as cattle and sheep.

This invention also includes methods for using compounds of Formula I to treat diseases or disorders in patients in which mediation by NK-3 receptors and/or GABA$_A$ receptors is of importance.

Preferred compounds of this invention are ligands for neurokinin and GABA receptors, in particular NK-3 receptors and/or GABA$_A$ receptors, and are useful in the treatment of a wide range of diseases or disorders of the central nervous system (CNS) and periphery in mammals in which modulation of NK-3 receptors and/or GABA$_A$ receptors is of importance. These include depression, anxiety, panic disorder, obsessive compulsive disorder, psychosis and schizophrenia, sleep disorders, cognitive disorders, low alertness, psychosis and schizophrenia, neurodegenerative disorders such as dementia, Alzheimer's diseases, Parkinson's disease, Huntington's disease, Down's syndrome, benzodiazepine overdoses, stress related somatic disorders, reflex sympathetic dystrophy, dysthmic disorders, obesity, eating disorders, drug and alcohol addiction, movement disorders, convulsive disorders such as epilepsy, migraine, headache, multiple sclerosis and other demyelinating diseases, AIDS related neuropathy, chemotherapy-induced neuropathy and neuralgia, diabetic or peripheral neuropathy, neurogenic inflammation, inflammatory pain, neuropathic pain, and other types of chronic or acute pain, Reynaud's disease, vasodilation, vasospasm, angina, asthma, chronic obstructive pulmonary diseases, airway hyperreactivity, cough, allergic rhinitis, bronchospasm, bronchopneumonia, ocular inflammation, inflammatory bowel disease, Crohn's disease, ulcerative colitis, biliary disfunction, skin disorders and itch, hypersensitivity disorders, atopic dermatitis, contact dermatitis, cutaneous wheal and flare, renal disorders, urinary incontinence, immune system disorders and adverse immunological reactions, fibrositis, osteoarthritis, eosino-philic fascioliasis, and scleroderma. Compounds contained in the invention are also useful for the diagnosis of disorders involving mediation by neurokinin NK-3 receptors and/or GABA$_A$ receptors in patients.

Non-toxic pharmaceutical salts include salts, include, but not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, pamoate, salicylate and stearate. Similarly, pahrmaceutically acceptable cations include, but are not limited to sodium, potassium, calcium, aluminum, lithium and ammonium.

The present invention also encompasses the prodrugs of the compounds of Formula I. Those skilled in the art will recognize various synthetic methodologies (references by N. Bodor, Drugs of the Future, 1981, 6, 165–182, or H. Bundgaard, Advanced Drug Delivery Reviews, 1989, 3, 39–65) which may be employed to prepare non-toxic pharmaceutically acceptable prodrugs of the compounds encompassed by Formula I.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of schizophrenia, depression, cognitive deficity or anxiety a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to NK-3 and/or $GABA_A$ receptor modulation, e.g., treatment schizoprenia, depression, or chronic pulmonary obstructive disorder by NK-3 receptor modulation or treatment of sleep disorders, cognitive deficits, anxiety or depression by $GABA_A$ receptor modulation. The packaged pharmaceutical compositions include a container holding a therapeutically effective amount of at least one NK-3 and/or $GABA_A$ receptor modulator as described supra and instructions (e.g., labeling) indicating the the contained NK-3 and/or $GABA_A$ receptor ligand is to be used for treating a disorder responsive to NK-3 and/or $GABA_A$ receptor modulation in the patient.

The present invention also pertains to methods of inhibiting the binding of neurokinin to the NK-3 receptor which methods involve contacting a compound of the invention with cells expressing NK-3 receptors, wherein the compound is present at a concentration sufficient to inhibit neurokinin binding to cells expressing a cloned human NK-3 receptor in vitro and to method for altering the signaltranducing activity of NK-3 receptors, said method comprising exposing cells expressing such receptor to an effective amount of a compound of the invention.

Preferred compounds of the invention show selectivity for the NK-3 Receptor or the $GABA_A$ receptor as measured by standard assays for NK-3 and $GABA_A$ Receptor binding (See example 41 for a standard assay of NK-3 receptor binding and example 43 for a standard assay of $GABA_A$ receptor binding).

Preferred compounds of the invention are those that show selectivity for the NK-3 receptor over the $GABA_A$ receptor and exhibit a 10-fold greater affinity for the NK-3 receptor; more preferred compounds exhibit a 100-fold greater affinity for the NK-3 receptor; and most preferred compounds exhibit a 1000-fold greater affinity for the NK-3 receptor in a standard assay of NK-3 receptor binding than for the $GABA_A$ receptor in a standard assay of $GABA_A$ receptor binding.

Preferred compounds of the invention are those that show selectivity for the $GABA_A$ receptor over the NK-3 receptor and exhibit a 10-fold greater affinity for the $GABA_A$ receptor, more preferred compounds exhibit a 100-fold greater affinity for the $GABA_A$ receptor, and most preferred compounds exhibit a 1000-fold greater affinity for the $GABA_A$ receptor in a standard assay of $GABA_A$ receptor binding than for the NK-3 receptor in a standard assay of Nk-3 receptor binding.

Compound Preparation

Several methods for preparing the compounds of this invention are illustrated in the following Scheme I, II and III. The synthesis of compounds of Formula II is described in detail in the several publications including Giardina et. al. J. Med. Chem. 1997, 40, 1794–1807 and Giardina et. al. J. Heterocyclic Chem., 1997, 34, 557–559 and references cited therein. It will be recognized by those skilled in the art that the structures of Formula III, IV, and V can be readily synthesized from various readily available amino acids. Alternatively, various readily available ketones and aldeydes can be converted to the corresponding aminocyanides and cyanohydrins and subsequently reduced to the desired diamines and aminoalcohols. Those skilled in the art will recognize that in certain instances it will be necessary to utilize compounds of Formula II and Formula III bearing protecting groups and that these groups can be removed in a subsequent reaction to yield compounds of Formula I as described in "Protective Groups in Organic Synthesis", 2nd Ed., Greene, T. W. and related publications.

Scheme I

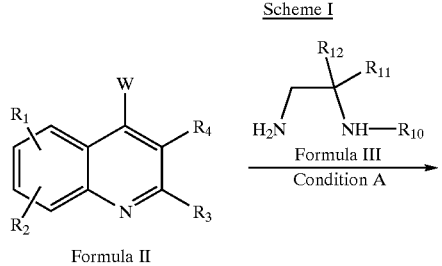

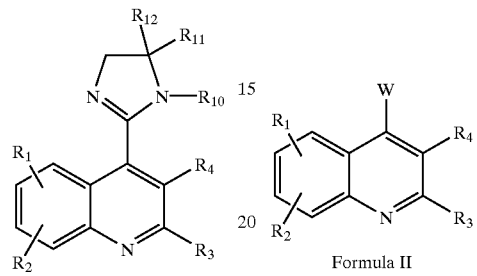

wherein $R_1$, $R_2$, $R_3$, $R_4$, $R_{10}$, $R_{11}$, and $R_{12}$ are as defined above, W is —$CO_2H$, —$CO_2Me$, —$CO_2Et$, —C(OEt)$_3$, —C=NHOMe, —C=NHOEt, —CSNH$_2$, —C=NHNH$_2$, or —CN.

Condition A includes, but is not limited to, heating with or without a solvent such as toluene, ethanol, or xylene at 40–250° C.; heating with AlMe$_3$ in a solvent such as toluene at 80–120° C. and, ocassionally, continued heating in the presence of Lawesson's reagent; or stirring at room temperature in presence of triphenylphosphine, CCl$_4$ and a base such as triethylamine or diisoprpylethylamine in a solvent such as acetonitrile or a mixture of solvents such as acetonitrile-pyridine.

Scheme II

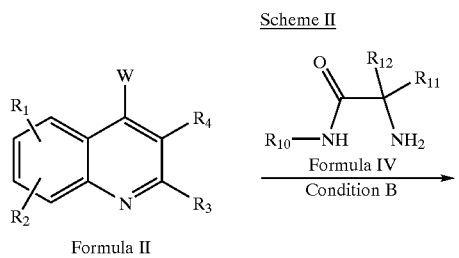

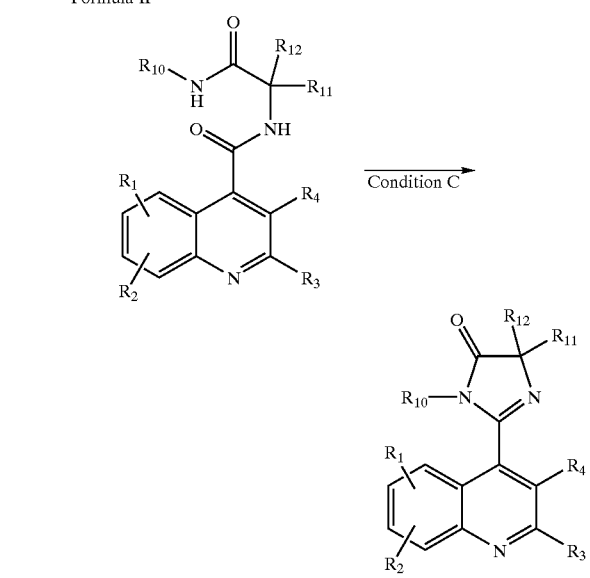

wherein $R_1$, $R_2$, $R_3$, $R_4$, $R_{10}$, $R_{11}$, and $R_{12}$ are as defined above, W is —COCl or —CO$_2$H.

Condition B includes, but is not limited to, reaction of the amine with acid chloride (W=COCl) in the presence of base as well as amide bond forming conditions such as those employing the BOP reagent in the presence of base.

Condition C includes, but is not limited to, treatment with sodium methoxide in the presence of methanol as solvent.

Scheme III

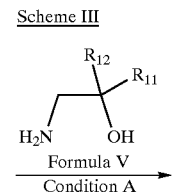

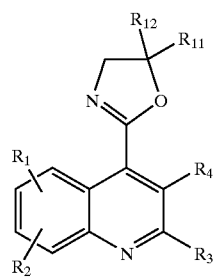

wherein $R_1$, $R_2$, $R_3$, $R_4$, $R_{11}$, $R_{12}$ are as defined above, W is —$CO_2H$, —$CO_2Me$, —$CO_2Et$, —C(OEt)$_3$, —C=NHOMe, —C=NHOEt, —CSNH$_2$, or —C=NHNH$_2$.

Condition A includes, but is not limited to, heating with or without a solvent such as toluene, ethanol, or xylene at 40–250° C.; heating with AlMe$_3$ in a solvent such as toluene at 80–120° C. and, ocassionally, continued heating in the presence of Lawesson's reagent; or stirring at room temperature in presence of triphenylphosphine, CCl$_4$ and a base such as triethylamine or diisoprpylethylamine in a solvent such as acetonitrile or a mixture of solvents such as acetonitrile-pyridine.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be obvious to those skilled in the art of organic synthesis as well as the conditions necessary to attach and remove such groups.

The invention is illustrated further by the following examples which are not to be construed as limiting the invention in scope or spirit to the specific procedures described in them.

EXAMPLE 1

5-Ethyl-5-phenyl-2-(3-methoxy-2-phenylquinolin-4-yl)-imidazoline.

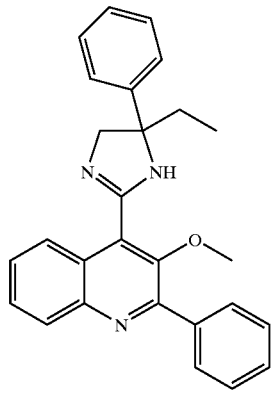

Step 1. 2-Amino-2-phenylbutanenitrile

A mixture of propiophenone (30 g), KCN (34.5 g) and $NH_4Cl$ (30 g) in 180 mL of conc. $NH_4OH$ and 120 mL of EtOH is stirred at ambient temperature for 4 days. The reaction mixture is concentrated under vacuum and ether was added to the solid residue. The ether suspension is filtered and solid is washed with ether. Excess 1M of HCl in ether is added to the filtrate to precipitate HCl salt. The white solid is collected by filtration, washed with hexane and ether, and dried to give 29 g of the title compound as HCl salts. The white solid is basified with excess aqueous $NaHCO_3$ and extracted with $CH_2Cl_2$. The extract is washed with brine, dried and concentrated to give 19 g of the titled compound as clear oil.

Step 2. 2-Phenylbutane-1,2-diamine

To a stirred suspension of lithium aluminum hydride (LAH, 7.0 g) in 250 mL of ether is added dropwise a solution of the compound of step 1(10.0 g) in 10 mL of ether at $-70°$ C. The reaction mixture is stirred at $-60°$ C. to $-70°$ C. until TLC (10% MeOH in $CH_2Cl_2$) shows the disappearance of the starting material. The excess LAH is destroyed by cautious addition of a saturated aqueous $Na_2SO_4$ solution. The resulting mixture is filtered and solid is washed with EtOAc. The filtrate is dried over $Na_2SO_4$ and concentrated under vacuum to give 8.3 g of the title compound as clear oil.

Step 3. N-(2-Amino-2-phenylbutyl)-3-methoxy-2-phenylquinoline-4-carboxamide

A mixture of 3-methoxy-2-phenylquinoline-4-carboxylic acid (3.0 g), and the compound of step 2 (3.0 g), BOP (5.7 g) and TEA (2.0 g) in 25 mL of anhydrous DMF is stirred at ambient temperature overnight. The mixture is diluted with water and EtOAc. The organic layer is separated, washed with water and concentrated under vacuum. The residue is purified on a silica gel column, eluting with EtOAc and Hexane (1:1) to afford the title compound as white foam.

Step 4. (R,S)-4-Ethyl-4-phenyl-2-(3-methoxy-2-phenylquinolin-4-yl)-imidazoline Triphenylphospine (4.3 g) is added once to a mixture of the compound of step 3 (2.3 g), TEA (1.6 mL), CCl4 (3.1 mL), pyridine (20 mL) and acetonitrile (20 mL). The reaction mixture is stirred at ambient temperature overnight. It is then evaporated and mixed with EtOAc and aqueous $Na_2CO_3$ solution. The organic layer is separated, and washed with brine and evaporated. The residue is purified on a silica gel column, eluting with EtOAc and Hexane (from 1:4 to 1:1) to afford the titled compound as white foam. HCl salt is prepared by addition of HCl in ether to a solution of free base in EtOAc and filtration.

LC-MS data: HPLC: 2.18 min (HPLC method: YMC-pack pro $C_{18}$ column, 33×4.6 mm(L×ID), 5 μm particle size. 3 min gradient from 5% to 95% B with 0.5 min hold at 95% B. Solvent A: 95% $H_2O$-5% MeOH-0.05% TFA; Solvent B: 95% MeOH-5% $H_2O$-0.05% TFA). Flow rate=2.0 ml/min. Injection volume=1 μl. MS ($ES^+$): m/e 408 $[MH]^+$.

Enantiomers of Example 1 are separated by Chiral HPLC column. Peak 1: retention time=6.507 min (99.47% e.e.). Peak 2: retention time=10.497 min (99.23% e.e.). Separation method: Chiral HPLC column: CHIRALPAK® AD, 250× 4.6 mm (L×ID), 20 μm particle size. Eluent: Hexane/Ethanol/DEA=90/10/0.1 (v/v/v). Flow rate=2.0 ml/min. P=11 kg/$cm^2$. Injection volume=5 μl.

EXAMPLE 2

4-Ethyl-4-phenyl-2-(2-phenylquinolin-4-yl)-imidazoline

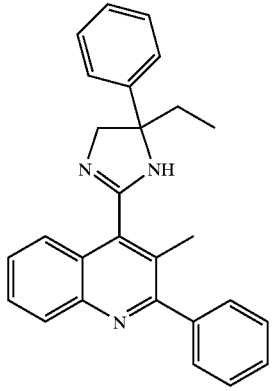

2-Phenylbutane-1,2-diamine (328 mg, 2.0 mmol) in 4.4 mL of toluene is added dropwise to a stirred solution of trimethylaluminum (2.0 M, 1 mL) in 5 mL of toluene at below 10° C. under nitrogen. At the end of methane evolution, methyl-2-phenyl-4-quinolinecarboxylate (263 mg, 1 mmol) in 2 mL of toluene is gradually added at room temperature. The reaction mixture is refluxed for 3 hours under nitrogen. After cooling, the solution is treated with 1 mL of water, diluted with 1 mL of methanol and 1 mL of methylene chloride, and refluxed for 15 minutes. After separation of organic solvent and solvent evaporation, the residue is purified over silica gel chromatography eluting with 5–10% MeOH/$CH_2Cl_2$. The corresponding compound is obtained as a white solid.

LC-MS data (same conditions as given in example 1): HPLC: 2.13, MS ($ES^+$): m/e 392 $[MH]^+$.

EXAMPLES 3–20

The following compounds are prepared by methods analogous to that of Example 1. LC-MS data are given as HPLC retention times and $[MH]^+$. The HPLC retention times of Table 1 are obtained by the method given in Example 1.

TABLE 1

| Example No. | Structure | Compound Name | HPLC time (min) | [MH]+ |
|---|---|---|---|---|
| 3 | 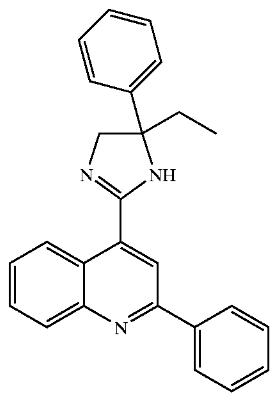 | 5-Ethyl-5-phenyl-2-(2-phenylquinolin-4-yl)-imidazoline | 2.23 | 378 |
| 4 | 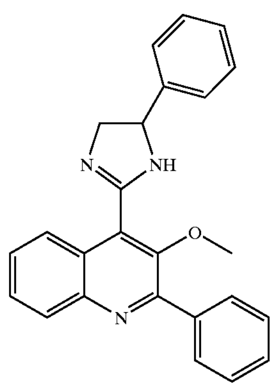 | 5-phenyl-2-(3-methoxy-2-phenylquinolin-4-yl)-imidazoline | 2.12 | 380 |
| 5 | 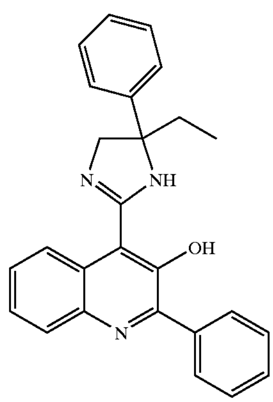 | 5-Ethyl-5-phenyl-2-(3-hydroxy-2-phenylquinolin-4-yl)-imidazoline | N/A | 394 |

TABLE 1-continued

| Example No. | Structure | Compound Name | HPLC time (min) | [MH]+ |
|---|---|---|---|---|
| 6 | 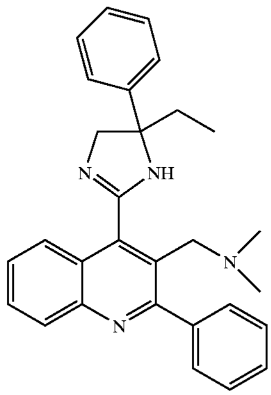 | 5-Ethyl-5-phenyl-2-[3-(dimethylamino)methyl-2-phenylquinolin-4-yl]-imidazoline | 1.92 | 435 |
| 7 | 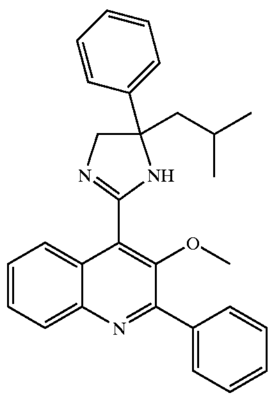 | 5-Isobutyl-5-phenyl-2-(3-methoxy-2-phenylquinolin-4-yl)-imidazoline | 2.29 | 437 |
| 8 | 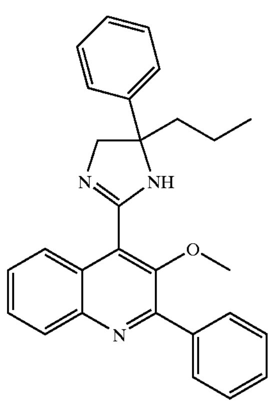 | 5-Propyl-5-phenyl-2-(3-methoxy-2-phenylquinolin-4-yl)-imidazoline | 2.24 | 422 |

TABLE 1-continued

| Example No. | Structure | Compound Name | HPLC time (min) | [MH]+ |
|---|---|---|---|---|
| 9 | 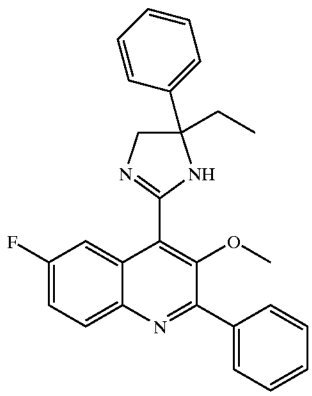 | 5-Ethyl-5-phenyl-2-(6-fluoro-3-methoxy-2-phenylquinolin-4-yl)-imidazoline | 2.21 | 426 |
| 10 | 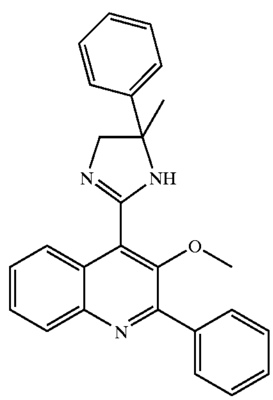 | 5-Methyl-5-phenyl-2-(3-methoxy-2-phenylquinolin-4-yl)-imidazoline | 2.15 | 394 |
| 11 | 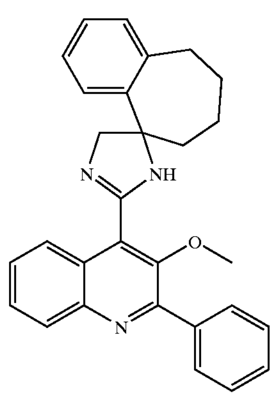 | 2'-(3-methoxy-2-phenylquinolin-4-yl)-spiro[6,7,8,9-tetrahydro-5H-benzocycloheptene-5,4'-imidazoline] | 2.26 | 434 |

TABLE 1-continued

| Example No. | Structure | Compound Name | HPLC time (min) | [MH]+ |
|---|---|---|---|---|
| 12 | 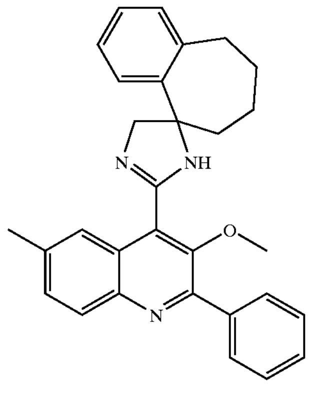 | 2'-(3-methoxy-6-methyl-2-phenylquinolin-4-yl)-spiro[6,7,8,9-tetrahydro-5H-benzocycloheptene-5,4'-imidazoline] | 2.31 | 448 |
| 13 | 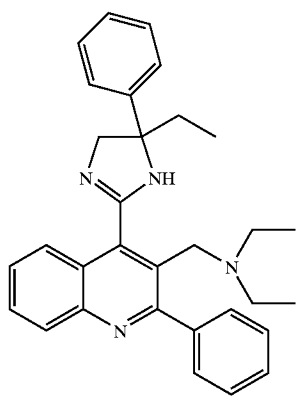 | 5-Ethyl-5-phenyl-2-[(3-(diethylamino)methyl-2-phenylquinolin-4-yl]-imidazoline | 1.97 | 463 |
| 14 | 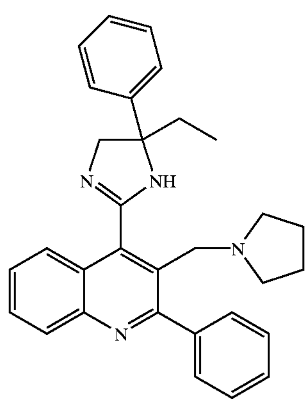 | 5-Ethyl-5-phenyl-2-[3-(1-pyrrolidinyl)methyl-2-phenylquinolin-4-yl]-imidazoline | 1.96 | 461 |

TABLE 1-continued

| Example No. | Structure | Compound Name | HPLC time (min) | [MH]+ |
|---|---|---|---|---|
| 15 | 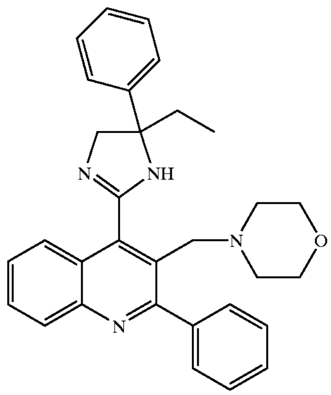 | 5-Ethyl-5-phenyl-2-[3-(4-morpholinyl)methyl-2-phenylquinolin-4-yl]-imidazoline | 2.13 | 477 |
| 16 | 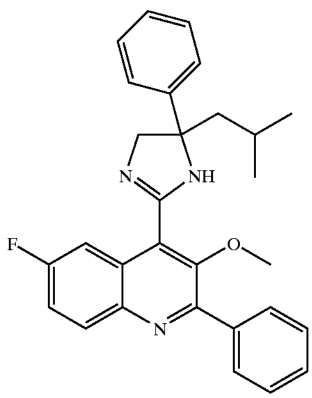 | 5-Isobutyl-5-phenyl-2-(6-fluoro-3-methoxy-2-phenylquinolin-4-yl)-imidazoline | 2.32 | 454 |
| 17 | 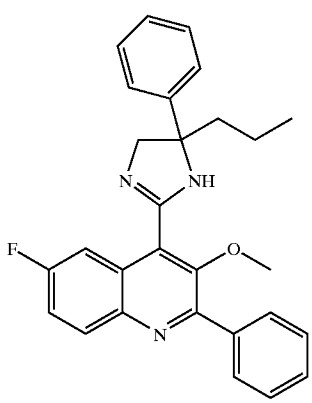 | 5-Propyl-5-phenyl-2-(6-fluoro-3-methoxy-2-phenylquinolin-4-yl)-imidazoline | 1.61 | 348 |

TABLE 1-continued

| Example No. | Structure | Compound Name | HPLC time (min) | [MH]+ |
|---|---|---|---|---|
| 18 | 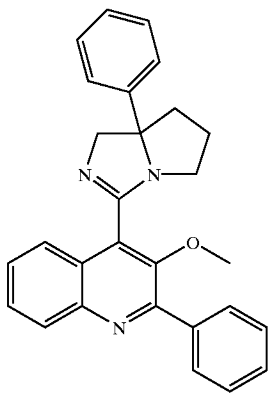 | 3-(3-methoxy-2-phenylquinolin-4-yl)-7a-phenyl-5,6,7,7a-tetrahydro-1H-pyrrolo[1,2-c]imidazole | 2.30 | 420 |
| 19 | 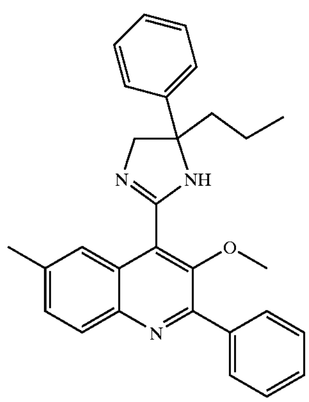 | 5-Propyl-5-phenyl-2-(6-methyl-3-methoxy-2-phenylquinolin-4-yl)-imidazoline | 2.29 | 436 |
| 20 | 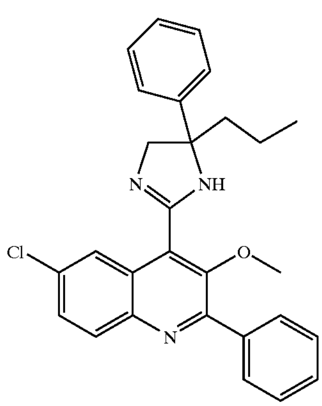 | 5-Propyl-5-phenyl-2-(6-chloro-3-methoxy-2-phenylquinolin-4-yl)-imidazoline | 2.35 | 456 |

TABLE 1-continued
| Example No. | Structure | Compound Name | HPLC time (min) | [MH]+ |
|---|---|---|---|---|
| 21 | 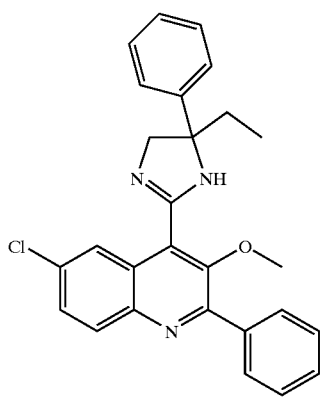 | 5-Ethyl-5-phenyl-2-(6-chloro-3-methoxy-2-phenylquinolin-4-yl)-imidazoline | 2.29 | 442 |
| 22 | 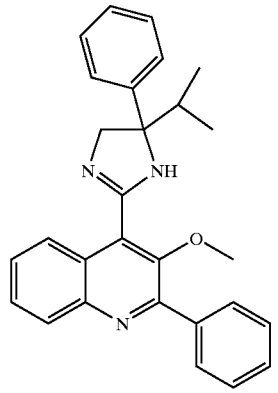 | 5-Isopropyl-5-phenyl-2-(3-methoxy-2-phenylquinolin-4-yl)-imidazoline | 2.21 | 422 |
| 23 | 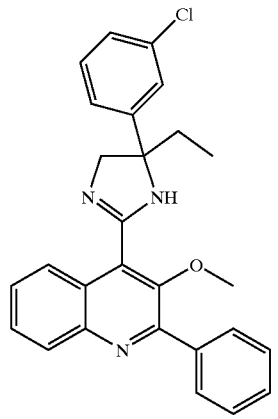 | 5-Ethyl-5-(3-chlorophenyl)-2-(3-methoxy-2-phenylquinolin-4-yl)-imidazoline | 2.29 | 442 |

TABLE 1-continued

| Example No. | Structure | Compound Name | HPLC time (min) | [MH]+ |
|---|---|---|---|---|
| 24 | 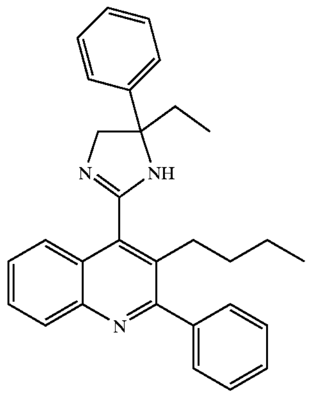 | 5-Ethyl-5-phenyl-2-(3-butyl-2-phenylquinolin-4-yl)-imidazoline | 2.33 | 444 |
| 25 | 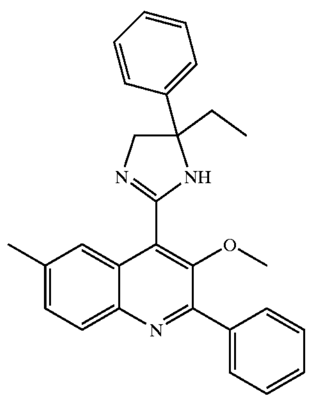 | 5-Ethyl-5-phenyl-2-(3-methoxy-6-methyl-2-phenylquinolin-4-yl)-imidazoline | 2.24 | 422 |
| 26 | 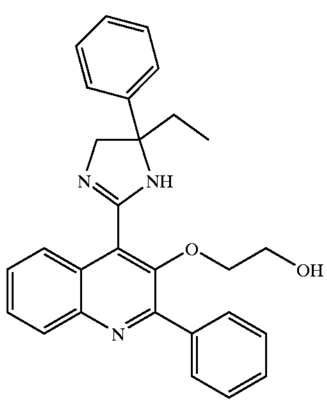 | 5-Ethyl-5-phenyl-2-[3-(2-hydroxyethoxy-2-phenylquinolin-4-yl]-imidazoline | 2.10 | 438 |

TABLE 1-continued

| Example No. | Structure | Compound Name | HPLC time (min) | [MH]+ |
|---|---|---|---|---|
| 27 | 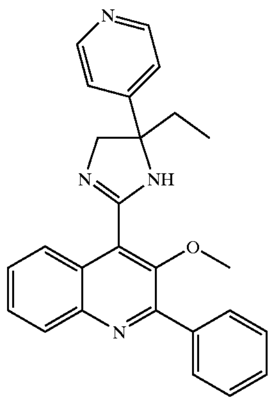 | 5-Ethyl-5-(4-pyridinyl)-2-(3-methoxy-2-phenylquinolin-4-yl)-imidazoline | 1.83 | 409 |
| 28 | 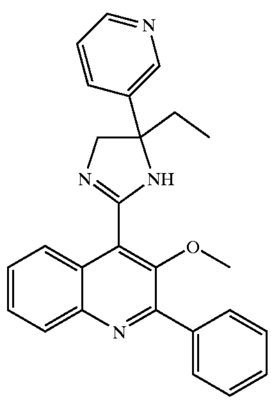 | 5-Ethyl-5-(3-pyridinyl)-2-(3-methoxy-2-phenylquinolin-4-yl)-imidazoline | 1.91 | 409 |
| 29 | 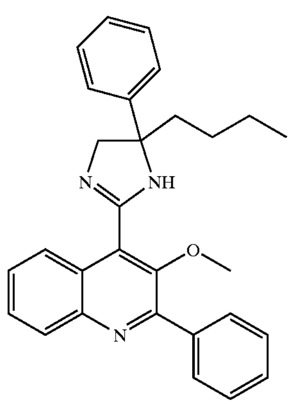 | 5-Butyl-5-phenyl-2-(3-methoxy-2-phenylquinolin-4-yl)-imidazoline | 2.31 | 436 |

TABLE 1-continued

| Example No. | Structure | Compound Name | HPLC time (min) | [MH]+ |
|---|---|---|---|---|
| 30 | 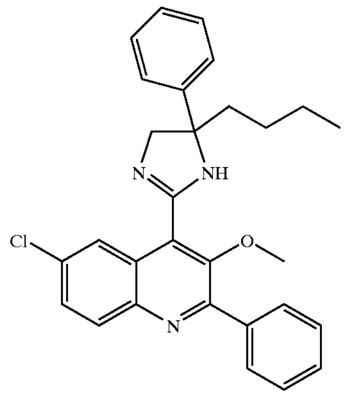 | 5-Butyl-5-phenyl-2-(6-chloro-3-methoxy-2-phenylquinolin-4-yl)-imidazoline | 2.39 | 471 |
| 31 | 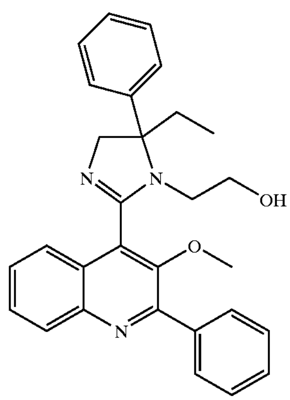 | 1-(2-Hydroxyethoxy)-5-ethyl-5-phenyl-2-(3-methoxy-2-phenylquinolin-4-yl)-imidazoline | 2.12 | 452 |
| 32 | 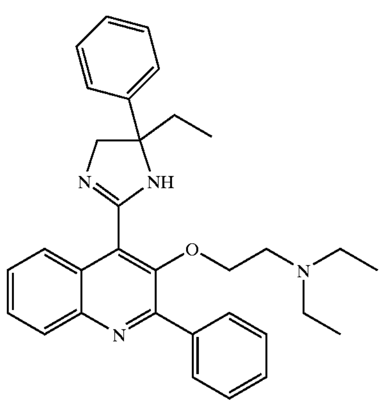 | 5-Ethyl-5-phenyl-2-{3-[2-(diethylamino)ethoxy]-2-phenylquinolin-4-yl}-imidazoline | N/A | 493 |

TABLE 1-continued

| Example No. | Structure | Compound Name | HPLC time (min) | [MH]+ |
|---|---|---|---|---|
| 33 | 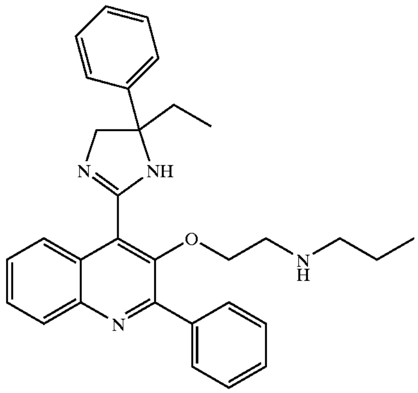 | 5-Ethyl-5-phenyl-2-{3-[2-(propylamino)ethoxy]-2-phenylquinolin-4-yl}-imidazoline | N/A | 479 |
| 34 | 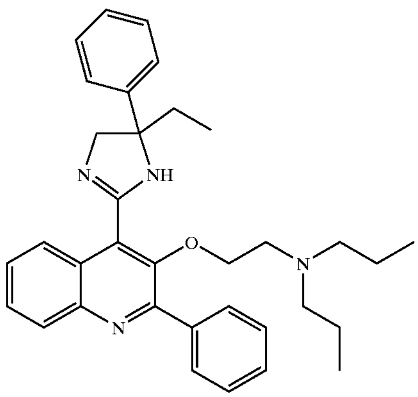 | 5-Ethyl-5-phenyl-2-{3-[2-(dipropylamino)ethoxy]-2-phenylquinolin-4-yl}-imidazoline | N/A | 521 |
| 35 | 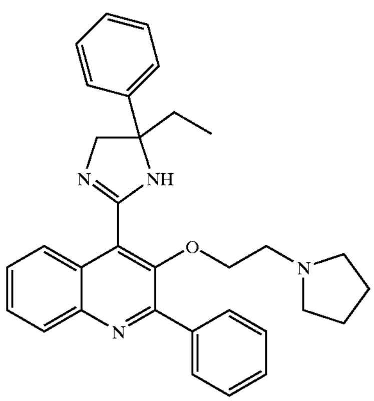 | 5-Ethyl-5-phenyl-2-{3-[2-(1-pyrrolidinyl)ethoxy]-2-phenylquinolin-4-yl}-imidazoline | N/A | 491 |
| 36 | 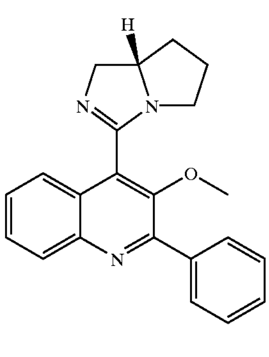 | S-3-(3-Methoxy-2-phenylquinolin-4-yl)-5,6,7,7a-tetrahydro-1H-pyrrolo[1,2-c]imidazoline | N/A | 314 |

TABLE 1-continued

| Example No. | Structure | Compound Name | HPLC time (min) | [MH]+ |
|---|---|---|---|---|
| 37 | 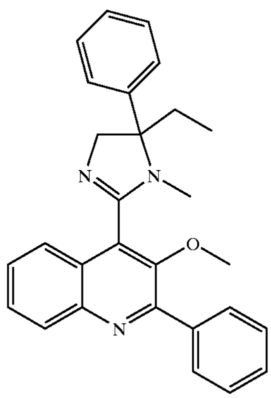 | 5-Ethyl-1-methyl-5-phenyl-2-(3-methoxy-2-phenylquinolin-4-yl)-imidazoline | N/A | 422 |

Example 38

4-Ethyl-4-phenyl-2-(2-phenylquinolin-4-yl)-imidazolin-5-one

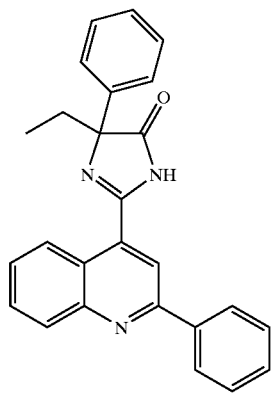

To a solution of 2-phenylquinolinecarboxylic acid (600 mg, 2.4 mmol) in 10 mL of $CH_2Cl_2$ containing 1 mL of triethylamine is added BOP (1.3 g, 2.9 mmol) followed by 2-amino-2-phenylbutanamide (500 mg, 2.8 mmol). The reaction mixture is stirred overnight at room temperature. The mixture is diluted with 20 mL of $CH_2Cl_2$, then washed with aqueous $Na_2CO_3$, aqueous citric acid and brine. After drying over $Na_2SO_4$, the solvent is evaporated to afford N-(1-Carbamoyl-1-phenylpropyl)-2-phenyl-4-quinolinecarboxamide (700 mg) as a pale yellow foam.

A mixture of N-(1-Carbamoyl-1-phenylpropyl)-2-phenyl-4-quinolinecarboxamide (100 mg, 0.24 mmol) and MeONa (13.2 mg, 0.24 mmol) in 5 mL of MeOH is refluxed for 4 hours. After cyclization is complete, the mixture is cooled and neutralized with HCl in MeOH and solvent is evaporated. The residue is washed with water and dried. Trituration with ethyl acetate affords the corresponding compound as a white solid.

LC-MS data (same condition as given in example 1): HPLC: 2.86 min. MS (ES+): m/e 392 [MH]+.

EXAMPLE 39

2-(3-Methoxy-2-phenylquinolin-4-yl)-5-phenyl-5-propyl-2-oxazoline

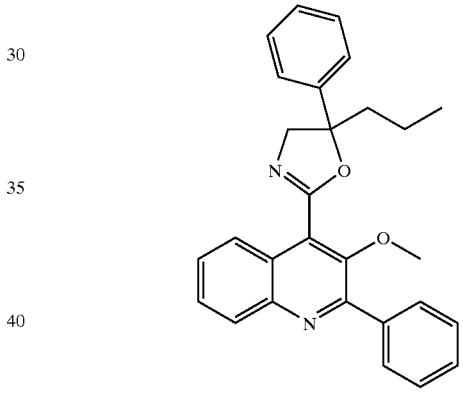

Triphenylphosphine (2.10 g, 8.0 mmol) is added to a mixture of (3-methoxy-2-phenylquinolin-4-yl)carboxylic acid (0.61 g, 2.2 mmol), pyridine (anhydrous, 5 mL), acetonitrile (anhydrous, 5 mL), triethylamine (1.4 mL, 10 mmol), 1-amino-2-phenyl-2-pentanol (0.40 g, 2.2 mmol), and carbon tetrachloride (1.5 mL, 16 mmol) stirred under nitrogen at ambient temperature. After stirring for 1 h without heating, the mixture is stirred at 40° C. for 2 h. The reaction mixture is dissolved in chloroform (100 mL). The solution is washed with 10% acetic acid (100 mL) followed by 5% sodium bicarbonate (100 mL) and dried over sodium carbonate. The solvent is evaporated under reduced pressure. The crude product is subjected to column chromatography on silica gel using chloroform-diethyl ether (49:1) and then to preparative TLC using hexanes-diethyl ether (3:1) as an eluent to give the titled compound (160 mg, 17%). $^1$H NMR (CDCl$_3$) δ0.93(t, J=7.5 Hz, 3 H), 1.32 (m, 1 H), 1.48 (m, 1 H), 2.13 (m, 2 H), 3.60 (s, 3 H), 4.35 (d, J=14.6 Hz, 1 H), 4.40 (d, J=14.6 Hz, 1 H), 7.31 (tt, J=7.1 and 1.5 Hz, 1 H), 7.40 (t, J=7.4 Hz, 2 H), 7.43–7.56 (m, 6 H), 7.67 (ddd, J=8.2, 6.9 and 1.5 Hz, 1 H) 7.96 (dd, J=8.4 and 1.5 Hz, 1 H), 8.07 (m, 2 H), 8.17 (d, J=8.5 Hz, 1 H). LC-MS data (same condition as given in example 1): HPLC: 2.62 min. MS (ES+): m/e 407 [MH]+.

EXAMPLE 40

2-(3-Methyl-2-phenylquinolin-4-yl)-5-phenyl-5-propyl-2-oxazoline

Following essentially the procedure of Example 39, (3-methy-2-phenylquinolin-4-yl)carboxylic acid and 1-amino-2-phenyl-2-pentanol are converted to the titled compound.

LC-MS data (same condition as given in example 1): HPLC: 2.78 min. MS (ES$^+$): m/e 423 [MH]$^+$.

EXAMPLE 41

Assay for NK-3 Recptor Binding Activity

The following assay is a standard assay for NK-3 receptor binding activity. Assays are performed as described in Krause et al (Proc. Natl. Acad. Sci. USA 94: 310–315, 1997). The NK-3 receptor complementary DNA is cloned from human hypothalamic RNA using standard procedures. The receptor cDNA is inserted into the expression vector pM$^2$ to transfect the mammalian Chinese hamster ovary cell line, and a stably expressing clonal cell line is isolated, characterized and used for the current experiments. Cells are grown in minimal essential medium alpha containing 10% fetal bovine serum and 250 µg/ml G418. Cells are liberated from cell culture plates with No-zyme (PBS base, JRH Biosciences), and harvested by low speed centrifugation. The cell pellet is homogenized in TBS (0.05 m TrisHCl, 120 mM NaCl, pH 7.4) with a Polytron homogenizer at setting 5 for 20 seconds, and total cellular membranes are isolated by centrifugation at 47,500×g for 10 minutes. The membrane pellet is resuspended by homogenization with the Polytron as above, and the membranes are then isolated by centrifugation at 47,500×g for 10 minutes. This final membrane pellet is resuspended in TBS at a protein concentration of 350 µg/ml.

Receptor binding assays contain a total volume of 200 µl containing 50 µg membrane protein, 0.05–0.15 nM 125I-methylPhe7-neurokinin B, drug or blocker in TBS containing 1.0 mg/ml bovine serum albumen, 0.2 mg/ml bacitracin, 20 µg/ml leupeptin and 20 µg/ml chymostatin. Incubations are carried out for 2 hours at 4° C., and the membrane proteins are harvested by passing the incubation mixture by rapid filtration over presoaked GF/B filters to separate bound from free ligand. The filters are presoaked in TBS containing 2% BSA and 0.1% Tween 20. After filtration of the incubation mixture, filters are rinsed 4 times with ice-cold TBS containing 0.01% sodium dodecyl sulfate and radioactivity is quantitated in a β-plate scintillation counter. One µM methylPhe7-neurokinin B is added to some tubes to determine nonspecific binding. Data are collected in duplicate determinations, averaged, and the percent inhibition of total specific binding is calculated. The total specific binding is the total binding minus the nonspecific binding. In many cases, the concentration of unlabeled drug is varied and total displacement curves of binding is carried out. Data are converted to a form for the calculation of IC$_{50}$ and Hill coefficient (nH). Binding data for compounds of this invention are listed in Table 2.

TABLE 2

| Example | IC$_{50}$(nM) |
|---|---|
| 1 | 19 |
| 2 | 0.3 |

EXAMPLE 42

Assay for NK-3 Functional Activity

Calcium Mobilization Assays: The human NK-3 bearing Chinese hamster ovary cells are grown in minimal essential media supplemented with 250 ug/ml G418, 10% fetal bovine serum and 25 mM Hepes, pH=7.4. Forty eight hours prior to the day of assay, the cells are plated in fresh media that does not contain the G418. On the day of assay, cells grown to 70–90% confluency in 96-well plates are washed with Krebs-Ringer buffer (25 mM HEPES, 5 mM KCl, 0.96 mM NaH$_2$PO$_4$. 1 mM MgSO$_4$, 2 mM CaCl$_2$, 5 mM glucose, 1 mM probenecid, pH 7.4) and are then incubated for 1–2 hours in the above buffer supplemented with Fluo3-AM (2.5 to 10 µg/ml; Teflabs) at 37 degrees C. in an environment containing 5% CO$_2$. The wells are then washed twice with Krebs Ringers HEPES buffer. Agonist-induced (methylPhe7-neurokinin B) calcium mobilization is monitored using a FLIPR (Molecular Devices) instrument. The agonist is added to the cells and fluorescence responses are continuously recorded for up to 5 min. For the examination of antagonist drug candidates, compounds are preincubated with the cells for up to 30 min. prior to administration of the methylPhe7-neurokinin B agonist usually at a concentration that brings about a 50% maximal activity. Responses are recorded for times up to 5 min. Kaleidagraph software (Synergy Software, Reading, Pa.) is utilized to fit the data to the equation y=a*(1/(1+(b/x)c)) to determine the EC$_{50}$ value or IC$_{50}$ value for the response. In this equation, y is the maximum fluorescence signal, x is the concentration of the agonist or antagonist, a is the E$_{max}$, b corresponds to the EC$_{50}$ or IC$_{50}$ value, and, finally, c is the Hill coefficient.

EXAMPLE 43

Assay for GABA$_A$ Receptor Binding

The following assay is a standard assay for GABA$_A$ receptor binding.

The high affinity and high selectivity of compounds of this invention for the benzodiazepine site of the GABA$_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at –20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containi 100 µl of tissue homogenate, 100 µl of radioligand, (0.5 nM $^3$H-Ro15-1788 [$^3$H-Flumazenil], specific activity 80 Ci/mmol), and test compound or control (see below), and are brought to a total volume of 500 µl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}$M to $10^{-5}$M obtained per curve by the method described above for determining percent inhibition. $K_i$ values are calculated according the Cheng-Prussof equation. When tested in this assay compounds of the invention exihibit $K_i$ values of less than 1 µM, preferred compounds of the invention have $K_i$ values of less than 500 nM and more compounds of the invention have $K_i$ values of less than 100 nM.

EXAMPLE 44

Assay for $GABA_A$ Receptor Functional Activity Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and Whiter Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human al, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evokable GABA current (e.g. 1 µM–9 µM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 µM RO15-1788, followed by exposure to GABA+1 µM RO15-1788+ test compound. Percent change due to addition of compound is calculated as described above. Any percent change observed in the presence of RO15-1788 is subtracted from the percent changes in current amplitude observed in the absence of 1 µM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

EXAMPLE 45

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^3$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 46

Use of Compounds of the Invention as Probes for NK-3 and/or $GABA_A$ Receptors in Cultured Cells and Tissue Samples Receptor autoradiography (receptor mapping) of NK-3 or $GABA_A$ receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

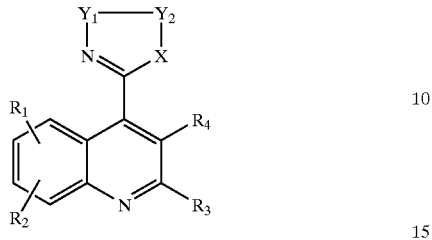

or a pharmaceutically acceptable salt or a pharmaceutically acceptable solvate thereof, wherein:

$R_1$ is selected from:
hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N ($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO ($C_{1-6}$ alkyl), or —SO$_2$($C_{1-6}$ alkyl),
wherein said $C_{1-6}$ alkyl may be straight, branched or cyclic, may contain one or two double or triple bonds, and is unsubstituted or substituted with one or more substituents selected from: hydroxy, oxo, fluoro, amino, $C_{1-3}$ alkoxy;

$R_2$ and $R_3$ are independently selected from the groups consisting of:

(1) $C_{1-8}$ alkyl, wherein said $C_{1-8}$ alkyl is straight, branched or cyclic, may contain one or two double or triple bonds, and is unsubstituted or substituted with one or more of the substituents selected from:
(i) hydroxy,
(ii) oxo,
(iii) fluoro,
(iv) amino,
(v) Ar$_1$, wherein Ar$_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from
hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein $C_{1-6}$ alkyl, is defined as above,
(vi) —NR$_5$R$_6$, wherein R$_5$ and R$_6$ are independently selected at each occurrence from:
(a) hydrogen,
(b) $C_{1-6}$ alkyl, wherein $C_{1-6}$ alkyl is as defined above,
(c) —(CH$_2$)n—Ar$_1$, wherein n is independently selected at each occurence from 0, 1 or 2,
or the groups $R_5$ and $R_6$ are joined together to form a 4- to 8-membered ring and may contain one or two double bonds, or one or two oxo, or one or two O, S or N—R$_7$ wherein R$_7$ is independently selected at each occurrence from hydrogen, $C_{1-6}$ alkyl, —(CH$_2$)n—Ar$_1$,
(vii) —OR$_5$, wherein R$_5$ is as defined above,
(viii) —CONR$_5$R$_6$ wherein R$_5$ and R$_6$ are as defined above,
(ix) —CO$_2$R$_5$, wherein said R$_5$ is as defined above;

(2) Ar$_2$, wherein Ar$_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), wherein said $C_{1-8}$ alkyl is as defined above;

(3) —NR$_8$R$_9$, wherein R$_8$ and R$_9$ are independently selected at each occurrence from:
(a) hydrogen,
(b) Ar$_2$,
(c) $C_{1-8}$ alkyl, wherein said $C_{1-8}$ alkyl is as defined above;
or the groups R$_8$ and R$_9$ may be joined together to form a 4- to 8-membered ring of which the 4- to 8-membered ring may contain one or more double bonds; one or more oxo; one or more O, S(O)n, N—R$_7$ wherein n and R$_7$ are as defined above; one or more groups consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO ($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$ ($C_{1-8}$ alkyl), (4) —OR$_8$;

R$_4$ is selected from:
hydrogen, halogen, hydroxy, $C_{1-8}$ alkyl, —O($C_{1-8}$ alkyl), —O($C_1$–$C_6$ alkyl)N($C_1$–$C_6$ alkyl)($C_1$–$C_6$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$(C$_{1-8}$ alkyl), —S(C$_{1-8}$ alkyl), —SO(C$_{1-8}$ alkyl), —SO$_2$(C$_{1-8}$ alkyl), or Ar$_2$;

X is NH, O or N—R$_{10}$, wherein R$_{10}$, is C$_{1-8}$ alkyl, or hydroxy C$_1$–C$_6$)alkoxy; and Y$_1$ is —CR$_{11}$R$_{12}$—, —CR$_{11}$R$_{12}$(CH$_2$)$_p$—, —(CH$_2$)$_p$CR$_{11}$R$_{12}$—, or —(CH$_2$)$_p$CO—, where p is 0, 1, or 2; and Y$_2$ is —CR$_{11}$'R$_{12}$'— or —CO— with the proviso that Y$_2$ is not —CO— when Y$_1$ is —(CH$_2$)$_p$CO—, where
  R$_{11}$ is selected from
    (1) hydrogen,
    (2) C$_{1-8}$ alkyl,
    (3) —CONR$_8$R$_9$ wherein R$_8$ and R$_9$ are as defined above,
    (4) —CO$_2$R$_8$, wherein said R$_8$ is as defined above; and R$_{11}$' is selected from
    (2) C$_{2-8}$ alkyl,
    (3) —CONR$_8$R$_9$ wherein R$_8$ and R$_9$ are as defined above,
    (4) —CO$_2$R$_8$, wherein said R$_8$ is as defined above; and
  R$_{12}$ and R$_{12}$' independently represent C$_1$–C$_6$ alkyl or Ar$_3$, where
    Ar$_3$ carries the definition of Ar$_2$, provided that not more than one of R$_{12}$ and R$_{12}$' is Ar$_3$;
  or one of R$_{11}$ or R$_{11}$' is an alkylene group attached to Ar$_3$ forming a 5-, 6-, or 7-membered carbocyclic ring with Ar$_3$;
  or when X is N—R$_{10}$, the groups R$_{10}$ and R$_{11}$' together with the atoms to which they are attached form a 5- to 8-membered ring, where the 5- to 8-membered ring optionally contains
    one or more double bonds;
    one or more oxo;
    one or more O, S(O)n, N—R$_7$ wherein n and R$_7$ are as defined above; or
  where the 5- to 8-membered ring is optionally substituted with one or more groups independently selected from the group consisting of hydroxy, halogen, amino, C$_{1-8}$ alkyl, —O(C$_{1-8}$ alkyl), —NO$_2$, —CN, —SO$_2$NH$_2$, —SO$_2$NH(C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —N(C$_{1-8}$ alkyl)CO$_2$(C$_{1-8}$ alkyl), —NHSO$_2$(C$_{1-8}$ alkyl), —N(C$_{1-8}$ alkyl)SO$_2$(C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl), —SO(C$_{1-8}$ alkyl).

2. A compound according to claim 1, or a pharmaceutically acceptable salt or solvate thereof, wherein X is NH or N—R$_{10}$.

3. A compound or salt according to claim 1, wherein
  R$_{11}$ and R$_{12}$ are both hydrogen;
  X is NR$_{10}$; and
  R$_1$ and R$_2$ are attached at the 6 and 7 positions of the quinoline ring respectively.

4. A compound or pharmaceutically acceptable salt according to claim 3, wherein:
  R$_2$ is hydrogen;
  R$_3$ is phenyl trisubstituted with R$_a$, R$_b$, and R$_c$ and R$_{12}$ is phenyl trisubstituted with R$_f$, R$_g$, and R$_h$,
    where each of R$_a$, R$_b$, R$_c$, R$_f$, R$_g$, and R$_h$ independently represent hydrogen, halogen, hydroxy, C$_{1-6}$ alkyl, —O(C$_{1-6}$ alkyl), —NO$_2$, —CN, —SO$_2$NH$_2$, amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —CON(C$_{1-6}$ alkyl)(C$_{1-6}$ alkyl), —CO$_2$(C$_{1-6}$ alkyl);
  R$_{11}$' is a straight or branched chain alkyl having from 2 to 8 carbon atoms, or straight or branched chain alkoxy; and
  R$_{10}$ is hydrogen, methyl or ethyl.

5. A compound or salt according to claim 4, wherein R$_4$ is C$_1$–C$_6$ alkoxy.

6. A compound or salt according to claim 5, wherein R$_1$ is hydrogen.

7. A compound or salt according to claim 1, wherein
  R$_1$ is attached at the 6-position of the quinoline ring;
  X is N—R$_{10}$, wherein R$_{10}$ is hydrogen, methyl, or ethyl;
  either R$_{11}$ and R$_{12}$ or R$_{11}$' and R$_{12}$' together with the carbon atom to which they are attached form a 5-, 6-, or 7-membered carbocyclic ring.

8. A compound according to claim 7, wherein
  R$_3$ is phenyl substituted with R$_a$, R$_b$, and R$_c$, where R$_a$, R$_b$, and R$_c$ independently represent hydrogen, halogen, hydroxy, C$_{1-6}$ alkyl, —O(C$_{1-6}$ alkyl), —NO$_2$, —CN, —SO$_2$NH$_2$, amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —CON(C$_{1-6}$ alkyl)(C$_{1-6}$ alkyl), —CO$_2$(C$_{1-6}$ alkyl);
  R$_4$ is selected from:
    hydrogen, halogen, hydroxy, C$_{1-8}$ alkyl, —O(C$_{1-8}$ alkyl), —O(C$_1$–C$_6$ alkyl)N(C$_1$–C$_6$ alkyl)(C$_1$–C$_6$ alkyl), —NO$_2$, —CN, —SO$_2$NH$_2$, —SO$_2$NH(C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —N(C$_{1-8}$ alkyl)CO$_2$(C$_{1-8}$ alkyl), —NHSO$_2$(C$_{1-8}$ alkyl), —N(C$_{1-8}$ alkyl)SO$_2$(C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl), —SO(C$_{1-8}$ alkyl), —SO$_2$(C$_{1-8}$ alkyl), and Ar$_2$;
  R$_{10}$ is hydrogen, methyl or ethyl;
  R$_{11}$ and R$_{12}$ are hydrogen; and
  R$_{12}$' is phenyl.

9. A compound according to claim 1, wherein
  R$_{11}$ and R$_{12}$ are hydrogen;
  R$_{12}$' is phenyl substituted with R$_f$, R$_g$, and R$_h$, and R$_3$ is phenyl substituted with R$_a$, R$_b$, and R$_c$, where R$_f$, R$_g$, R$_h$, R$_a$, R$_b$, and R$_c$ independently represent hydrogen, halogen, hydroxy, C$_{1-6}$ alkyl, —O(C$_{1-6}$ alkyl), —NO$_2$, —CN, —SO$_2$NH$_2$, amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —CON(C$_{1-6}$ alkyl)(C$_{1-6}$ alkyl), —CO$_2$(C$_{1-6}$ alkyl).

10. A compound of the formula:

or a pharmaceutically acceptable salt or solvate thereof wherein z is 1, 2 or 3;

$R_p$ is one or more groups independently selected from the group consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl);

$R_1$ is selected from:

hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein said $C_{1-6}$ alkyl is straight, branched or cyclic, may contain one or two double or triple bonds, and is unsubstituted or substituted with one or more substituents selected from hydroxy, oxo, fluoro, amino, $C_{1-3}$ alkoxy;

$R_2$ and $R_3$ are independently selected from the groups consisting of:

(1) hydrogen or $C_{1-8}$ alkyl, wherein said $C_{1-8}$ alkyl is straight, branched or cyclic, may contain one or two double or triple bonds, and is unsubstituted or substituted with one or more of the substituents selected from:

(i) hydroxy,
(ii) oxo,
(iii) fluoro,
(iv) amino,
(v) Ar$_1$, wherein Ar$_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein $C_{1-6}$ alkyl, is defined as above, (vi) —NR$_5$R$_6$, wherein R$_5$ and R$_6$ are independently selected at each occurrence from:

(a) hydrogen,
(b) $C_{1-6}$ alkyl, wherein $C_{1-6}$ alkyl is as defined above,
(c) —(CH$_2$)n—Ar$_1$, wherein n is independently selected at each occurrence from 0, 1 or 2, or the groups R$_5$ and R$_6$ are joined together to form a 4- to 8-membered ring and may contain one or two double bonds, or one or two oxo, or one or two O, S or N—R$_7$ wherein R$_7$ is independently selected at each occurrence from hydrogen, $C_{1-6}$ alkyl, —(CH$_2$)n—Ar$_1$, (vii) —OR$_5$, wherein R$_5$ is as defined above,
(viii) —CONR$_5$R$_6$ wherein R$_5$ and R$_6$ are as defined above,
(ix) —CO$_2$R$_5$, wherein said R$_5$ is as defined above;

(2) Ar$_2$, wherein Ar$_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:

hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), wherein said $C_{1-8}$ alkyl is as defined above;

(3) —NR$_8$R$_9$, wherein R$_8$ and R$_9$ are independently selected at each occurrence from:

(a) hydrogen,
(b) Ar$_2$,
(c) $C_{1-8}$ alkyl, wherein said $C_{1-8}$ alkyl is as defined above;

or the groups R$_8$ and R$_9$ are joined together to form a 4- to 8-membered ring of which the 4- to 8-membered ring may contain one or more double bonds; one or more oxo; one or more O, S(O)n, N—R$_7$ wherein n and R$_7$ are as defined above; one or more groups consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), (4) —OR$_8$;

$R_4$ is selected from:

hydrogen, halogen, hydroxy, $C_{1-8}$ alkyl, —O($C_{1-8}$ alkyl), —O($C_1$–$C_6$ alkyl)N($C_1$–$C_6$ alkyl)($C_1$–$C_6$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-6}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), —SO$_2$($C_{1-8}$ alkyl), and Ar$_2$;

$Y_1$ is —CR$_{11}$R$_{12}$—, —CR$_{11}$R$_{12}$(CH$_2$)$_p$—, —(CH$_2$)$_p$CR$_{11}$R$_{12}$—, or —(CH$_2$)$_p$CO—, where p is 0, 1, or 2; and $R_{11}$ is
(1) hydrogen,
(2) $C_{1-8}$ alkyl,
(3) $Ar_2$,
(4) —$CONR_8R_9$ wherein $R_8$ and $R_9$ are as defined above,
(5) —$CO_2R_8$, wherein $R_8$ is as defined above; and $R_{12}$ and $R_{12}'$ independently represent hydrogen, $C_1$-$C_8$ alkyl, —$CONR_8R_9$ wherein $R_8$ and $R_9$ are as defined above, —$CO_2R_8$ wherein said $R_8$ is as defined above, or $Ar_3$, where $Ar_3$ carries the definition of $Ar_2$, provided that one and only one of $R_{12}$ and $R_{12}'$ is $Ar_2$.

11. A compound according to claim 10, wherein
$Y_1$ is —$CR_{11}R_{12}$— where both $R_{11}$ and $R_{12}$ represent hydrogen;
$R_{12}'$ is hydrogen, $C_1$–$C_6$ alkyl, or phenyl;
z is 1; and
$R_p$ is hydrogen.

12. A compound according to claim 11, wherein $R_1$ and $R_2$ are attached to the 6- and 7-positions of the quinoline ring, respectively.

13. A compound according to claim 12, wherein
$R_1$ and $R_2$ are hydrogen;
$R_3$ is phenyl substituted with $R_a$, $R_b$, and $R_c$, where each of $R_a$, $R_b$, and $R_c$ is independently selected from hydrogen, halogen, hydroxy, $C_{1-6}$ alkyl, —$O(C_{1-6}$ alkyl), —$NO_2$, —CN, —$SO_2NH_2$, amino, —$NH(C_{1-6}$ alkyl), —$N(C_{1-6}$ alkyl)($C_{1-6}$ alkyl), —$N(C_{1-6}$ alkyl)CO($C_{1-6}$ alkyl), —$N(C_{1-6}$ alkyl)$CO_2(C_{1-6}$ alkyl), —CON($C_{1-6}$ alkyl)($C_{1-6}$ alkyl), —$CO_2(C_{1-6}$ alkyl); and
$R_4$ is $C_1$–$C_6$ alkoxy, hydroxy($C_1$–$C_6$)alkoxy, amino, or mono- or di($C_1$–$C_6$) alkylamino.

14. A compound according to claim 13, wherein $R_4$ is $C_1$–$C_6$ alkoxy.

15. A compound of the formula:

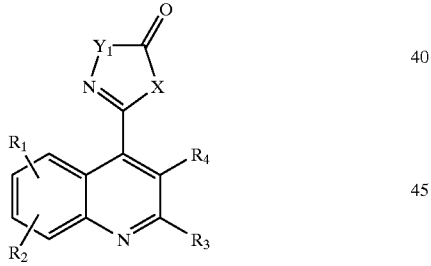

or a pharmaceutically acceptable salt or solvate thereof, where
$R_1$ is selected from:
hydrogen, halogen, hydroxy, $C_{1-6}$ alkyl, —$O(C_{1-6}$ alkyl), —$NO_2$, —CN, —$SO_2NH_2$, —$SO_2NH(C_{1-6}$ alkyl), —$SO_2N(C_{1-6}$ alkyl)($C_{1-6}$ alkyl), amino, —$NH(C_{1-6}$ alkyl), —$N(C_{1-6}$ alkyl)($C_{1-6}$ alkyl), —$N(C_{1-6}$ alkyl)CO($C_{1-6}$ alkyl), —$N(C_{1-6}$ alkyl)$CO_2$ ($C_{1-6}$ alkyl), —$NHSO_2(C_{1-6}$ alkyl), —$N(C_{1-6}$ alkyl)$SO_2(C_{1-6}$ alkyl), —$SO_2NHCO(C_{1-6}$ alkyl), —$CONHSO_2(C_{1-6}$ alkyl), —$CON(C_{1-6}$ alkyl)($C_{1-6}$ alkyl), —$CO_2(C_{1-6}$ alkyl), —$S(C_{1-6}$ alkyl), —SO ($C_{1-6}$ alkyl), or —$SO_2(C_{1-6}$ alkyl),
wherein said $C_{1-6}$ alkyl is straight, branched or cyclic, may contain one or two double or triple bonds, and is unsubstituted or substituted with one or more substituents selected from hydroxy, oxo, fluoro, amino, $C_{1-3}$ alkoxy;

$R_2$ and $R_3$ are independently selected from the groups consisting of:
(1) hydrogen or $C_{1-8}$ alkyl, wherein said $C_{1-8}$ alkyl is straight, branched or cyclic, may contain one or two double or triple bonds, and is unsubstituted or substituted with one or more of the substituents selected from:
(i) hydroxy,
(ii) oxo,
(iii) fluoro,
(iv) amino,
(v) $Ar_1$, wherein $Ar_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from
hydrogen, halogen, hydroxy, $C_{1-6}$ alkyl, —$O(C_{1-6}$ alkyl), —$NO_2$, —CN, —$SO_2NH_2$, —$SO_2NH(C_{1-6}$ alkyl), —$SO_2N(C_{1-6}$ alkyl) ($C_{1-6}$ alkyl), amino, —$NH(C_{1-6}$ alkyl), —$N(C_{1-6}$ alkyl)($C_{1-6}$ alkyl), —$N(C_{1-6}$ alkyl) CO($C_{1-6}$ alkyl), —$N(C_{1-6}$ alkyl)$CO_2(C_{1-6}$ alkyl), —$NHSO_2(C_{1-6}$ alkyl), —$N(C_{1-6}$ alkyl) $SO_2(C_{1-6}$ alkyl), —$SO_2NHCO(C_{1-6}$ alkyl), —$CONHSO_2(C_{1-6}$ alkyl), —$CON(C_{1-6}$ alkyl) ($C_{1-6}$ alkyl), —$CO_2(C_{1-6}$ alkyl), —$S(C_{1-6}$ alkyl), —$SO(C_{1-6}$ alkyl), or —$SO_2(C_{1-6}$ alkyl), wherein $C_{1-6}$ alkyl, is defined as above,
(vi) —$NR_5R_6$, wherein $R_5$ and $R_6$ are independently selected at each occurrence from:
(a) hydrogen,
(b) $C_{1-6}$ alkyl, wherein $C_{1-6}$ alkyl is as defined above,
(c) —$(CH_2)n$-$Ar_1$, wherein n is independently selected at each occurrence from 0, 1 or 2,
or the groups $R_5$ and $R_6$ are joined together to form a 4- to 8-membered ring and may contain one or two double bonds, or one or two oxo, or one or two O, S or N—$R_7$ wherein $R_7$ is independently selected at each occurrence from hydrogen, $C_{1-6}$ alkyl, —$(CH_2)n$—$Ar_1$,
(vii) —$OR_5$, wherein $R_5$ is as defined above,
(viii) —$CONR_5R_6$ wherein $R_5$ and $R_6$ are as defined above,
(ix) —$CO_2R_5$, wherein said $R_5$ is as defined above;
(2) $Ar_2$, wherein $Ar_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
hydrogen, halogen, hydroxy, $C_{1-8}$ alkyl, —$O(C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —$NH(C_{1-8}$ alkyl), —$N(C_{1-8}$ alkyl)($C_{1-8}$ alkyl), —$N(C_{1-8}$ alkyl)CO($C_{1-8}$ alkyl), —$N(C_{1-8}$ alkyl) $CO_2(C_{1-8}$ alkyl), —$NHSO_2(C_{1-8}$ alkyl), —$N(C_{1-8}$ alkyl)$SO_2(C_{1-8}$ alkyl), —$SO_2NHCO(C_{1-8}$ alkyl), —$CONHSO_2(C_{1-8}$ alkyl), —$CON(C_{1-8}$ alkyl) ($C_{1-8}$ alkyl), —$CO_2(C_{1-8}$ alkyl), —$S(C_{1-8}$ alkyl), —$SO(C_{1-8}$ alkyl), or —$SO_2(C_{1-8}$ alkyl), wherein said $C_{1-8}$ alkyl is as defined above;

57

(3) —NR$_8$R$_9$, wherein R$_8$ and R$_9$ are independently selected at each occurrence from:
  (a) hydrogen,
  (b) Ar$_2$,
  (c) C$_{1-8}$ alkyl, wherein said C$_{1-8}$ alkyl is as defined above;
  or the groups R$_8$ and R$_9$ together with the atoms to which they are attached form a 4- to 8-membered ring, where the 4- to 8-membered ring optionally contains
  one or more double bonds;
  one or more oxo;
  one or more O, S(O)n, or N—R$_7$ wherein n and R$_7$ are as defined above; or
  the 4- to 8-membered ring is optionally substituted with one or more groups selected from the group consisting of hydroxy, halogen, amino, C$_{1-8}$ alkyl, —O(C$_{1-8}$ alkyl), —NO$_2$, —CN, —SO$_2$NH$_2$, —SO$_2$NH(C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —N(C$_{1-8}$ alkyl)CO$_2$(C$_{1-8}$ alkyl), —NHSO$_2$(C$_{1-8}$ alkyl), —N(C$_{1-8}$ alkyl)SO$_2$(C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl), —SO(C$_{1-8}$ alkyl), or —SO$_2$(C$_{1-8}$ alkyl),
  (4) —OR$_8$;
R$_4$ is selected from:
  hydrogen, halogen, hydroxy, C$_{1-8}$ alkyl-O(C$_{1-8}$ alkyl), —NO$_2$, —CN, —SO$_2$NH$_2$, —SO$_2$NH(C$_{1-8}$ alkyl), —SO$_2$N(C$_{1-8}$ alkyl)(C$_{1-8}$ alkyl), amino, —NH(C$_{1-8}$ alkyl), —N(C$_{1-8}$ alkyl)(C$_{1-8}$ alkyl), —N(C$_{1-8}$ alkyl)CO(C$_{1-8}$ alkyl), —N(C$_{1-8}$ alkyl)CO$_2$(C$_{1-8}$ alkyl), —NHSO$_2$(C$_{1-8}$ alkyl), —N(C$_{1-6}$ alkyl)SO$_2$C$_{1-8}$ alkyl), —SO$_2$NHCO(C$_{1-8}$ alkyl), —CONHSO$_2$(C$_{1-8}$ alkyl), —CON(C$_{1-8}$ alkyl)(C$_{1-8}$ alkyl), —CO$_2$(C$_{1-8}$ alkyl), —S(C$_{1-8}$ alkyl), —SO(C$_{1-8}$ alkyl), —SO$_2$(C$_{1-8}$ alkyl), and Ar$_2$;
X is NH, O, or N—R$_{10}$, wherein R$_{10}$ is C$_{1-8}$ alkyl; and
Y$_1$ is —CR$_{11}$R$_{12}$—, —CR$_{11}$R$_{12}$(CH$_2$)$_p$—, or —(CH$_2$)$_p$CR$_{11}$R$_{12}$—, where p is 0, 1, or 2; and
R$_{11}$ and R$_{12}$ independently represent
  (1) hydrogen,
  (2) C$_{1-8}$ alkyl,
  (3) Ar$_2$,
  (4) —CONR$_8$R$_9$ wherein R$_8$ and R$_9$ are as defined above,
  (5) —CO$_2$R$_8$, wherein R$_8$ is as defined above.

16. A compound according to claim 15, wherein
X is NR$_{10}$;
R$_3$ is phenyl substituted with R$_a$, R$_b$, and R$_c$, where each of R$_a$, R$_b$, and R$_c$ is independently selected from hydrogen, halogen, hydroxy, C$_{1-6}$ alkyl, —O(C$_{1-6}$ alkyl), —NO$_2$, —CN, —SO$_2$NH$_2$, amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —CON(C$_{1-6}$ alkyl)(C$_{1-6}$ alkyl), —CO$_2$(C$_{1-6}$ alkyl); and
R$_{10}$ is hydrogen, methyl or ethyl.

17. A compound or salt according to claim 16, wherein
R$_1$ is attached at the 6-position of the quinoline ring;
R$_2$ is hydrogen; and
R$_{12}$ is phenyl substituted with R$_f$, R$_g$, and R$_h$, where each of R$_f$, R$_g$, and R$_h$ is independently selected from hydrogen, halogen, hydroxy, C$_{1-6}$ alkyl, —O(C$_{1-6}$

58 alkyl), —NO$_2$, —CN, —SO$_2$NH$_2$, amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —CON(C$_{1-6}$ alkyl)(C$_{1-6}$ alkyl), —CO$_2$(C$_{1-6}$ alkyl);
R$_{11}$ is hydrogen or straight or branched chain alkyl or straight or branched chain alkoxy.

18. A compound according to claim 17, wherein R$_1$ is hydrogen, and R$_{11}$ is hydrogen or C$_1$–C$_6$ alkyl.

19. A compound of the formula:

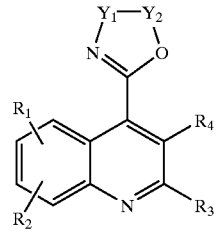

or a pharmaceutically acceptable salt or solvate thereof wherein:
R$_1$ is selected from:
  hydrogen, halogen, hydroxy, C$_{1-6}$ alkyl, —O(C$_{1-6}$ alkyl), —NO$_2$, —CN, —SO$_2$NH$_2$, —SO$_2$NH(C$_{1-6}$ alkyl), —SO$_2$N(C$_{1-6}$ alkyl)(C$_{1-6}$ alkyl), amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —NHSO$_2$(C$_{1-6}$ alkyl), —N(C$_{1-6}$ alkyl)SO$_2$(C$_{1-6}$ alkyl), —SO$_2$NHCO(C$_{1-6}$ alkyl), —CONHSO$_2$(C$_{1-6}$ alkyl), —CON(C$_{1-6}$ alkyl)(C$_{1-6}$ alkyl), —CO$_2$(C$_{1-6}$ alkyl), —S(C$_{1-6}$ alkyl), —SO (C$_{1-6}$ alkyl), or —SO$_2$(C$_{1-6}$ alkyl),
  wherein said C$_{1-6}$ alkyl is straight, branched or cyclic, may contain one or two double or triple bonds, and is unsubstituted or substituted with one or more substituents selected from hydroxy, oxo, fluoro, amino, C$_{1-3}$ alkoxy;
R$_2$ and R$_3$ are independently selected from the groups consisting of:
  (1) hydrogen or C$_{1-8}$ alkyl, wherein said C$_{1-8}$ alkyl is straight, branched or cyclic, may contain one or two double or triple bonds, and is unsubstituted or substituted with one or more of the substituents selected from:
    (i) hydroxy,
    (ii) oxo,
    (iii) fluoro,
    (iv) amino,
    (v) Ar$_1$, wherein Ar$_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from
      hydrogen, halogen, hydroxy, C$_{1-6}$ alkyl, —O(C$_{1-6}$ alkyl), —NO$_2$, —CN, —SO$_2$NH$_2$, —SO$_2$NH(C$_{1-6}$ alkyl), —SO$_2$N(C$_{1-6}$ alkyl)(C$_{1-6}$ alkyl), amino, —NH(C$_{1-6}$ alkyl), —N(C$_{1-6}$ alkyl)(C$_{1-6}$ alkyl), —N(C$_{1-6}$ alkyl)CO(C$_{1-6}$ alkyl), —N(C$_{1-6}$ alkyl)CO$_2$(C$_{1-6}$ alkyl), —NHSO$_2$(C$_{1-6}$ alkyl), —N(C$_{1-6}$ alkyl)SO$_2$(C$_{1-6}$ alkyl), —SO$_2$NHCO(C$_{1-6}$ alkyl), —CONHSO$_2$(C$_{1-6}$ alkyl), —CON(C$_{1-6}$ alkyl)

($C_{1-6}$ alkyl), —$CO_2$($C_{1-6}$ alkyl), —S($C_{1-6}$ alkyl), —SO($C_{1-6}$ alkyl), or —$SO_2$($C_{1-6}$ alkyl), wherein $C_{1-6}$ alkyl, is defined as above,
(vi) —$NR_5R_6$, wherein $R_5$ and $R_6$ are independently selected at each occurrence from:
  (a) hydrogen,
  (b) $C_{1-6}$ alkyl, wherein $C_{1-6}$ alkyl is as defined above,
  (c) —$(CH_2)n$—$Ar_1$, wherein n is independently selected at each occurrence from 0, 1 or 2,
 or the groups $R_5$ and $R_6$ are joined together to form a 4- to 8-membered ring and may contain one or two double bonds, or one or two oxo, or one or two O, S or N—$R_7$ wherein $R_7$ is independently selected at each occurrence from hydrogen, $C_{1-6}$ alkyl, —$(CH_2)n$—$Ar_1$,
(vii) —$OR_5$, wherein $R_5$ is as defined above,
(viii) —$CONR_5R_6$ wherein $R_5$ and $R_6$ are as defined above,
(ix) —$CO_2R_5$, wherein said $R_5$ is as defined above;
(2) $Ar_2$, wherein $Ar_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
  hydrogen, halogen, hydroxy, $C_{1-8}$ alkyl, —O($C_{1-8}$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl) ($C_{1-8}$ alkyl), —$CO_2$($C_{1-8}$ alkyl), —S($C_{1-8}$ alkyl), —SO($C_{1-8}$ alkyl), or —$SO_2$($C_{1-8}$ alkyl), wherein said $C_{1-8}$ alkyl is as defined above;
(3) —$NR_8R_9$, wherein $R_8$ and $R_9$ are independently selected at each occurrence from:
  (a) hydrogen,
  (b) $Ar_2$,
  (c) $C_{1-8}$ alkyl, wherein said $C_{1-8}$ alkyl is as defined above;
 or the groups $R_8$ and $R_9$ are joined together to form a 4- to 8-membered ring of which the 4- to 8-membered ring may contain one or more double bonds; one or more oxo; one or more O, S(O)n, N—$R_7$ wherein n and $R_7$ are as defined above; one or more groups consisting of hydroxy, halogen, amino, $C_{1-8}$ alkyl, —O($C_{1-8}$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl) ($C_{1-8}$ alkyl), —$CO_2$($C_{1-8}$ alkyl), —S($C_{1-8}$ alkyl), —SO($C_{1-8}$ alkyl), or —$SO_2$ ($C_{1-8}$ alkyl),
(4) —$OR_8$;
$R_4$ is selected from:
hydrogen, halogen, hydroxy, $C_{1-8}$ alkyl, —O($C_{1-8}$ alkyl), —O($C_1$–$C_6$ alkyl)N($C_1$–$C_6$ alkyl)($C_1$–$C_6$ alkyl), —$NO_2$, —CN, —$SO_2NH_2$, —$SO_2NH$($C_{1-8}$ alkyl), —$SO_2N$($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$ ($C_{1-8}$ alkyl), —$NHSO_2$($C_{1-8}$ alkyl), —N($C_{1-6}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO ($C_{1-8}$ alkyl), —$SO_2$($C_{1-8}$ alkyl), and $Ar_2$;
$Y_1$ is —$CR_{11}R_{12}$—, —$CR_{11}R_{12}(CH_2)_p$—, —$(CH_2)_p CR_{11}R_{12}$—, or —$(CH_2)_p CO$—, where p is 0, 1, or 2; and
$Y_2$ is —$CR_{11}'R_{12}'$— or —CO— with the proviso that $Y_2$ is not —CO— when $Y_1$ is —$(CH_2)_p CO$—,
where
  $R_{11}$, $R_{12}$, and $R_{12}'$ are independently selected from
    (1) hydrogen,
    (2) $Ar_2$,
    (3) $C_{1-8}$ alkyl,
    (4) —$CONR_8R_9$ wherein $R_8$ and $R_9$ are as defined above, and
    (5) —$CO_2R_8$, wherein said $R_8$ is as defined above; and
  $R_{11}'$ is selected from $C_{2-8}$ alkyl.
20. A compound according to claim 19, wherein $Y_1$ is —$CR_{11}R_{12}$— where both $R_{11}$ and $R_{12}$ represent hydrogen.
21. A compound according to claim 20, wherein
  $R_1$ and $R_2$ are attached at the 6 and 7 positions of the quinoline ring respectively;
  $R_3$ is phenyl substituted with $R_a$, $R_b$, and $R_c$, where $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl)($C_{1-6}$ alkyl), or —$CO_2$($C_{1-6}$ alkyl).
22. A compound according to claim 21, wherein:
  $R_2$ is hydrogen;
  $R_{12}'$ is phenyl substituted with $R_a$, $R_b$, and $R_c$, where $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl)($C_{1-6}$ alkyl), or —$CO_2$($C_{1-6}$ alkyl); and
  $R_{11}'$ is a straight or branched chain alkyl having 2 to 8 carbon atoms or straight or branched chain alkoxy.
23. A compound of the formula:

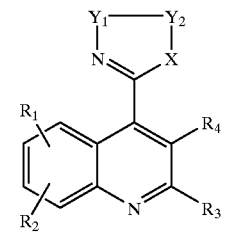

or a pharmaceutically acceptable salt or a pharmaceutically acceptable solvate thereof, wherein:
  $R_1$ is selected from:
    hydrogen, halogen, hydroxy, $C_{1-6}$ alkyl, —O($C_{1-6}$ alkyl), —$NO_2$, —CN, —$SO_2NH_2$, —$SO_2NH$($C_{1-6}$ alkyl), —$SO_2N$($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$ ($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein said $C_{1-6}$ alkyl is straight, branched or cyclic, may contain one or two double or triple bonds, and is unsubstituted or substituted with one or more substituents selected from hydroxy, oxo, fluoro, amino, $C_{1-3}$ alkoxy;

$R_2$ and $R_3$ are independently selected from the groups consisting of:

(1) hydrogen or $C_{1-8}$ alkyl, wherein said $C_{1-8}$ alkyl is straight, branched or cyclic, may contain one or two double or triple bonds, and is unsubstituted or substituted with one or more of the substituents selected from:
  (i) hydroxy,
  (ii) oxo,
  (iii) fluoro,
  (iv) amino,
  (v) Ar$_1$, wherein Ar$_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from
    hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein $C_{1-6}$ alkyl, is defined as above,
  (vi) —NR$_5$R$_6$, wherein R$_5$ and R$_6$ are independently selected at each occurrence from:
    (a) hydrogen,
    (b) $C_{1-6}$ alkyl, wherein $C_{1-6}$ alkyl is as defined above,
    (c) —(CH$_2$)n—Ar$_1$, wherein n is independently selected at each occurrence from 0, 1 or 2, or the groups R$_5$ and R$_6$ are joined together to form a 4- to 8-membered ring and may contain one or two double bonds, or one or two oxo, or one or two O, S or N—R$_7$ wherein R$_7$ is independently selected at each occurrence from hydrogen, $C_{1-6}$ alkyl, —(CH$_2$)n—Ar$_1$,
  (vii) —OR$_5$, wherein R$_5$ is as defined above,
  (viii) —CONR$_5$R$_6$ wherein R$_5$ and R$_6$ are as defined above,
  (ix) —CO$_2$R$_5$, wherein said R$_5$ is as defined above;

(2) Ar$_2$, wherein Ar$_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
    hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), wherein said $C_{1-8}$ alkyl is as defined above;

(3) —NR$_8$R$_9$, wherein R$_8$ and R$_9$ are independently selected at each occurrence from:
    (a) hydrogen,
    (b) Ar$_2$,
    (c) $C_{1-8}$ alkyl, wherein said $C_{1-8}$ alkyl is as defined above;
    or the groups R$_8$ and R$_9$ are joined together to form a 4- to 8-membered ring of which the 4- to 8-membered ring may contain one or more double bonds; one or more oxo; one or more O, S(O)n, N—R$_7$ wherein n and R$_7$ are as defined above; one or more groups consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), (4) —OR$_8$;

R$_4$ is selected from:
    halogen, hydroxy, —O($C_{1-8}$ alkyl), —O($C_1$–$C_6$ alkyl)N($C_1$–$C_6$ alkyl)($C_1$–$C_6$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-6}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), —SO$_2$($C_{1-8}$ alkyl), and Ar$_2$;

X is O or N—R$_{10}$, wherein R$_{10}$ is hydrogen, $C_1$–$C_6$ alkyl, or hydroxy ($C_1$–$C_6$) alkoxy; and Y$_1$ is —CR$_{11}$R$_{12}$—, —CR$_{11}$R$_{12}$(CH$_2$)$_p$—, —(CH$_2$)$_p$CR$_{11}$R$_{12}$—, or —(CH$_2$)$_p$CO—, where p is 0, 1, or 2; and Y$_2$ is —CR$_{11}$'R$_{12}$'— or —CO— with the proviso that Y$_2$ is not —CO— when Y$_1$ is —(CH$_2$)$_p$CO—, where
    R$_{11}$ and R$_{11}$' are independently selected from
    (1) hydrogen,
    (2) Ar$_2$,
    (3) $C_{1-8}$ alkyl,
    (4) —CONR$_8$R$_9$ wherein R$_8$ and R$_9$ are as defined above,
    (5) —CO$_2$R$_8$, wherein said R$_8$ is as defined above; and R$_{12}$ and R$_{12}$' independently represent hydrogen, $C_1$–$C_6$ alkyl, or Ar$_3$, where Ar$_3$ carries the definition of Ar$_2$;
provided that (1) one of R$_{12}$ and R$_{12}$' is Ar$_3$; and
one of R$_{11}$ or R$_{11}$' is an alkylene group attached to Ar$_3$ forming a 5-, 6-, or 7-membered carbocyclic ring with Ar$_3$ or (2) that both R$_{11}$' and R$_{12}$' are other than hydrogen.

24. A compound of the formula:

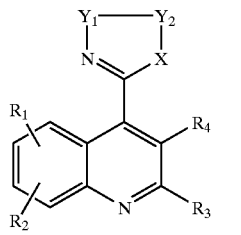

or a pharmaceutically acceptable salt or a pharmaceutically acceptable solvate thereof, wherein:

$R_1$ is selected from:
hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$ ($C_{1-6}$ alkyl), —NHSO$_2$($C_{1-6}$ alkyl), —N($C_{1-6}$ alkyl) SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO ($C_{1-6}$ alkyl), or —SO$_2$($C_{1-6}$ alkyl),
wherein said $C_{1-6}$ alkyl is straight, branched or cyclic, may contain one or two double or triple bonds, and is unsubstituted or substituted with one or more substituents selected from hydroxy, oxo, fluoro, amino, $C_{1-3}$ alkoxy;

$R_2$ and $R_3$ are independently selected from the groups consisting of:
(1) hydrogen or $C_{1-8}$ alkyl, wherein said $C_{1-8}$ alkyl is straight, branched or cyclic, may contain one or two double or triple bonds, and is unsubstituted or substituted with one or more of the substituents selected from:
(i) hydroxy,
(ii) oxo,
(iii) fluoro,
(iv) amino,
(v) Ar$_1$, wherein Ar$_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from
hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl) CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl) SO$_2$($C_{1-6}$ alkyl), —SO$_2$NHCO($C_{1-6}$ alkyl), —CONHSO$_2$($C_{1-6}$ alkyl), —CON($C_{1-6}$ alkyl) ($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein $C_{1-6}$ alkyl, is defined as above,
(vi) —NR$_5$R$_6$, wherein R$_5$ and R$_6$ are independently selected at each occurrence from:
(a) hydrogen,
(b) $C_{1-6}$ alkyl, wherein $C_{1-6}$ alkyl is as defined above,
(c) —(CH$_2$)n—Ar$_1$, wherein n is independently selected at each occurrence from 0, 1 or 2,
or the groups R$_5$ and R$_6$ are joined together to form a 4- to 8-membered ring and may contain one or two double bonds, or one or two oxo, or one or two O, S or N—R$_7$ wherein R$_7$ is independently selected at each occurrence from hydrogen, $C_{1-6}$ alkyl, —(CH$_2$)n—Ar$_1$,
(vii) —OR$_5$, wherein R$_5$ is as defined above,
(viii) —CONR$_5$R$_6$ wherein R$_5$ and R$_6$ are as defined above,
(ix) —CO$_2$R$_5$, wherein said R$_5$ is as defined above;
(2) Ar$_2$, wherein Ar$_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl) CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl) ($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), wherein said $C_{1-8}$ alkyl is as defined above;
(3) —NR$_8$R$_9$, wherein R$_8$ and R$_9$ are independently selected at each occurrence from:
(a) hydrogen,
(b) Ar$_2$,
(c) $C_{1-8}$ alkyl, wherein said $C_{1-8}$ alkyl is as defined above;
or the groups R$_8$ and R$_9$ are joined together to form a 4- to 8-membered ring of which the 4- to 8-membered ring may contain one or more double bonds; one or more oxo;
one or more O, S(O)n, N—R$_7$ wherein n and R$_7$ are as defined above; one or more groups consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$ ($C_{1-8}$ alkyl), —NHSO$_2$($C_{1-8}$ alkyl), —N($C_{1-8}$ alkyl) SO$_2$($C_{1-8}$ alkyl), —SO$_2$NHCO($C_{1-8}$ alkyl), —CONHSO$_2$($C_{1-8}$ alkyl), —CON($C_{1-8}$ alkyl) ($C_{1-8}$ alkyl), —CO$_2$($C_{1-8}$ alkyl), —S($C_{1-8}$ alkyl), —SO ($C_{1-8}$ alkyl), or —SO$_2$($C_{1-8}$ alkyl),
(4) —OR$_8$;

$R_4$ is selected from:
hydroxy or —O($C_{1-8}$ alkyl);

X is NH, O or N—R$_{10}$, wherein R$_{10}$ is $C_{1-8}$ alkyl or hydroxy($C_1$–$C_6$)alkoxy; and $Y_1$ is —CR$_{11}$R$_{12}$—, —CR$_{11}$R$_{12}$(CH$_2$)$_p$—, —(CH$_2$)$_p$ CR$_{11}$R$_{12}$—, or —(CH$_2$)$_p$CO—, where p is 0, 1, or 2; and $Y_2$ is —CR$_{11}$'R$_{12}$'— or —CO— with the proviso that Y$_2$ is not —CO— when Y$_1$ is —(CH$_2$)$_p$CO—, where
R$_{11}$ is selected from
(1) hydrogen, (2) $C_{1-8}$ alkyl, (3) —$CONR_8R_9$ wherein $R_8$ and $R_9$ are as defined above, (4) —$CO_2R_8$, wherein said $R_8$ is as defined above; and $R_{11}'$ is selected from (2) $C_{2-8}$ alkyl, (3) —$CONR_8R_9$ wherein $R_8$ and $R_9$ are as defined above, (4) —$CO_2R_8$, wherein said $R_8$ is as defined above; and $R_{12}$ and $R_{12}'$ independently represent hydrogen, $C_1$–$C_6$ alkyl, or $Ar_3$, where $Ar_3$ carries the definition of $Ar_2$, provided that not more than one of $R_{12}$ and $R_{12}'$ is $Ar_3$;

or one of $R_{11}$ or $R_{11}'$ is an alkylene group attached to $Ar_3$ forming a 5-, 6-, or 7-membered carbocyclic ring with $Ar_3$;

or when X is N—$R_{10}$, the groups $R_{10}$ and $R_{11}'$ together with the atoms to which they are attached form a 5- to 8-membered ring, where the 5- to 8-membered ring optionally contains one or more double bonds;

one or more oxo;

one or more O, S(O)n, N—$R_7$ wherein n and $R_7$ are as defined above; or where the 5- to 8-membered ring is optionally substituted with one or more groups independently selected from the group consisting of hydroxy, halogen, amino, $C_{1-8}$ alkyl, —O($C_{1-8}$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-8}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl).

25. A compound or pharmaceutically acceptable salt according to claim 3, wherein:

$R_2$ is hydrogen;

$R_3$ is phenyl trisubstituted with $R_a$, $R_b$, and $R_c$ and $R_{12}$ is phenyl trisubstituted with $R_f$, $R_g$, and $R_h$, where each of $R_a$, $R_b$, $R_c$, $R_f$, $R_g$, and $R_h$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl)($C_{1-6}$ alkyl), —$CO_2$($C_{1-6}$ alkyl);

$R_{11}'$ is a straight or branched chain alkyl having from 2 to 8 carbon atoms, or straight or branched chain alkoxy; and $R_{10}$ is hydrogen, methyl or ethyl.

26. A compound or salt according to claim 25, wherein $R_4$ is $C_1$–$C_6$ alkoxy.

27. A compound or salt according to claim 26, wherein $R_1$ is hydrogen.

28. A compound according to claim 26, wherein $R_3$ is phenyl substituted with $R_a$, $R_b$, and $R_c$, where $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl)($C_{1-6}$ alkyl), —$CO_2$($C_{1-6}$ alkyl);

$R_4$ is selected from:

hydrogen, halogen, hydroxy, $C_{1-8}$ alkyl, —O($C_{1-8}$ alkyl), —O($C_1$–$C_6$ alkyl)N($C_1$–$C_6$ alkyl)($C_1$–$C_6$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$($C_{1-8}$ alkyl), —$NHSO_2$($C_{1-8}$ alkyl), —N($C_{1-6}$ alkyl)$SO_2$($C_{1-8}$ alkyl), —$SO_2NHCO$($C_{1-8}$ alkyl), —$CONHSO_2$($C_{1-8}$ alkyl), —CON($C_{1-8}$ alkyl)($C_{1-8}$ alkyl), —$CO_2$($C_{1-8}$ alkyl), —S($C_{1-8}$ alkyl), —SO($C_{1-8}$ alkyl), —$SO_2$($C_{1-8}$ alkyl), and $Ar_2$;

$R_{10}$ is hydrogen, methyl or ethyl;

$R_{11}$ and $R_{12}$ are hydrogen; and $R_{12}'$ is phenyl.

29. A compound according to claim 24, wherein $R_{11}$ and $R_{12}$ are hydrogen;

$R_{12}'$ is phenyl substituted with $R_f$, $R_g$, and $R_h$, and $R_3$ is phenyl substituted with $R_a$, $R_b$, and $R_c$, where $R_f$, $R_g$, $R_h$, $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl)($C_{1-6}$ alkyl), —$CO_2$($C_{1-6}$ alkyl).

30. A compound of the formula:

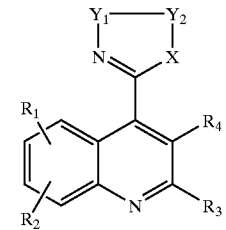

or a pharmaceutically acceptable salt or a pharmaceutically acceptable solvate thereof, wherein:

$R_1$ is selected from:

hydrogen, halogen, hydroxy, $C_{1-6}$ alkyl, —O($C_{1-6}$ alkyl), —$NO_2$, —CN, —$SO_2NH_2$, —$SO_2NH(C_{1-6}$ alkyl), —$SO_2N(C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —$NHSO_2$($C_{1-6}$ alkyl), —N($C_{1-6}$ alkyl)$SO_2$($C_{1-6}$ alkyl), —$SO_2NHCO$($C_{1-6}$ alkyl), —$CONHSO_2$($C_{1-6}$ alkyl), —CON($C_{1-6}$ alkyl)($C_{1-6}$ alkyl), —$CO_2$($C_{1-6}$ alkyl), —S($C_{1-6}$ alkyl), —SO($C_{1-6}$ alkyl), or —$SO_2$($C_{1-6}$ alkyl), wherein said $C_{1-6}$ alkyl is straight, branched or cyclic, may contain one or two double or triple bonds, and is unsubstituted or substituted with one or more substituents selected from hydroxy, oxo, fluoro, amino, $C_{1-3}$ alkoxy;

$R_2$ and $R_3$ are independently selected from the groups consisting of:

(1) hydrogen or $C_{1-8}$ alkyl, wherein said $C_{1-8}$ alkyl is straight, branched or cyclic, may contain one or two double or triple bonds, and is unsubstituted or substituted with one or more of the substituents selected from:

(i) hydroxy, (ii) oxo, (iii) fluoro, (iv) amino, (v) $Ar_1$, wherein $Ar_1$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, and benzopyrazolyl, each of which is unsubstituted or substituted with one or more substituents selected from hydrogen, halogen, hydroxy, $C_{1-6}$ alkyl, —O($C_{1-6}$ alkyl), —NO$_2$, —CN, —SO$_2$NH$_2$, —SO$_2$NH($C_{1-6}$ alkyl), —SO$_2$N($C_{1-6}$ alkyl)($C_{1-6}$ alkyl), amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)CO$_2$($C_{1-6}$ alkyl), —NHSO$_2$($C_{1-6}$ alkyl), —N($C_{1-6}$ alkyl)SO$_2$($C_{1-6}$ alkyl), —SO$_2$NHCO($C_{1-6}$ alkyl), —CONHSO$_2$($C_{1-6}$ alkyl), —CON($C_{1-6}$ alkyl)($C_{1-6}$ alkyl), —CO$_2$($C_{1-6}$ alkyl), —S($C_{1-6}$ alkyl), —SO($C_{1-6}$ alkyl), or —SO$_2$($C_{1-6}$ alkyl), wherein $C_{1-6}$ alkyl, is defined as above, (vi) —NR$_5$R$_6$, wherein R$_5$ and R$_6$ are independently selected at each occurrence from:
  (a) hydrogen,
  (b) $C_{1-6}$ alkyl, wherein $C_{1-6}$ alkyl is as defined above,
  (c) —(CH$_2$)n—Ar$_1$, wherein n is independently selected at each occurrence from 0, 1 or 2, or the groups R$_5$ and R$_6$ are joined together to form a 4- to 8-membered ring and may contain one or two double bonds, or one or two oxo, or one or two O, S or N—R$_7$ wherein R$_7$ is independently selected at each occurrence from hydrogen, $C_{1-6}$ alkyl, —(CH$_2$)n—Ar$_1$, (vii) —OR$_5$, wherein R$_5$ is as defined above,
(viii) —CONR$_5$R$_6$ wherein R$_5$ and R$_6$ are as defined above,
(ix) —CO$_2$R$_5$, wherein said R$_5$ is as defined above;

(2) Ar$_2$, wherein Ar$_2$ is independently selected at each occurrence from phenyl, naphthyl, thienyl, benzothienyl, pyridyl, quinolyl, pyrazinyl, pyrimidyl, imidazolyl, benzoimidazolyl, furanyl, benzofuranyl, thiazolyl, benzothiazolyl, isothiazolyl, benzisothiazolyl, triazolyl, tetrazolyl, pyrazolyl, or benzopyrazolyl, and unsubstituted or substituted with one or more substituents selected from:
hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), wherein said $C_{1-8}$ alkyl is as defined above;

(3) —NR$_8$R$_9$, wherein R$_8$ and R$_9$ are independently selected at each occurrence from:
(a) hydrogen,
(b) Ar$_2$,
(c) $C_{1-8}$ alkyl, wherein said $C_{1-8}$ alkyl is as defined above;
or the groups R$_8$ and R$_9$ are joined together to form a 4- to 8-membered ring of which the 4- to 8-membered ring may contain one or more double bonds; one or more oxo; one or more O, S(O)n, N—R$_7$ wherein n and R$_7$ are as defined above; one or more groups consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), (4) —OR$_8$;

R$_4$ is selected from:
hydrogen, halogen, hydroxy, $C_{1-8}$ alkyl, —O($C_{1-8}$ alkyl), —O($C_1$–$C_6$ alkyl)N($C_1$–$C_6$ alkyl)($C_1$–$C_6$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-6}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), —SO$_2$($C_{1-8}$ alkyl), and Ar$_2$;

X is NH, O or N—R$_{10}$, wherein R$_{10}$ is $C_{1-8}$ alkyl or hydroxy($C_1$–$C_6$)alkoxy; and Y$_1$ is —CR$_{11}$R$_{12}$—, —CR$_{11}$R$_{12}$(CH$_2$)$_p$—, —(CH$_2$)$_p$CR$_{11}$R$_{12}$—, or —(CH$_2$)$_p$CO—, where p is 0, 1, or 2; and Y$_2$ is —CR$_{11}$'R$_{12}$'— or —CO— with the proviso that Y$_2$ is not —CO— when Y$_1$ is —(CH$_2$)$_p$CO—, where
one of R$_{12}$ and R$_{12}$' is Ar$_3$ where Ar$_3$ is phenyl optionally substituted with hydrogen, halogen, hydroxy, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl), or —SO$_2$($C_{1-8}$ alkyl), and
the other of R$_{12}$ and R$_{12}$' is selected from hydrogen and $C_1$–$C_6$ alkyl,
one of R$_{11}$ or R$_{11}$' is hydrogen and the other is an alkylene group attached to Ar$_3$ forming a 5-, 6-, or 7-membered carbocyclic ring with Ar$_3$;
or when X is N—R$_{10}$, the groups R$_{10}$ and R$_{11}$' together with the atoms to which they are attached form a 5- to 8-membered ring, where the 5- to 8-membered ring optionally contains
one or more double bonds;
one or more oxo;
one or more O, S(O)n, N—R$_7$ wherein n and R$_7$ are as defined above; or
where the 5- to 8-membered ring is optionally substituted with one or more groups independently selected from the group consisting of hydroxy, halogen, amino, $C_{1-8}$ alkyl, —O($C_{1-8}$ alkyl), —NO$_2$, —CN, —SO$_2$NH$_2$, —SO$_2$NH($C_{1-8}$ alkyl), —SO$_2$N($C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)CO$_2$($C_{1-8}$ alkyl), —NHSO$_2$($C_{1-8}$ alkyl), —N($C_{1-8}$ alkyl)SO$_2$($C_{1-8}$ alkyl), —SO$_2$NHCO($C_{1-8}$ alkyl), —CONHSO$_2$($C_{1-8}$ alkyl), —CON($C_{1-8}$ alkyl)($C_{1-8}$ alkyl), —CO$_2$($C_{1-8}$ alkyl), —S($C_{1-8}$ alkyl), —SO($C_{1-8}$ alkyl).

31. A compound according to claim 30, or a pharmaceutically acceptable salt or solvate thereof, wherein X is NH or N—$R_{10}$.

32. A compound or salt according to claim 30, wherein
$R_{11}$ and $R_{12}$ are both hydrogen;
X is $NR_{10}$; and
$R_1$ and $R_2$ are attached at the 6 and 7 positions of the quinoline ring respectively.

33. A compound or pharmaceutically acceptable salt according to claim 32, wherein:
$R_2$ is hydrogen;
$R_3$ is phenyl trisubstituted with $R_a$, $R_b$, and $R_c$ and $R_{12}$ is phenyl trisubstituted with $R_f$, $R_g$, and $R_h$,
where each of $R_a$, $R_b$, $R_c$, $R_f$, $R_g$, and $R_h$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$ ($C_{1-6}$ alkyl), —CON($C_{1-6}$ alkyl)($C_{1-6}$ alkyl), —$CO_2$ ($C_{1-6}$ alkyl);
$R_{11}'$ is hydrogen, straight or branched chain alkyl, or straight or branched chain alkoxy; and
$R_{10}$ is hydrogen, methyl or ethyl.

34. A compound or salt according to claim 33, wherein $R_4$ is $C_1$–$C_6$ alkoxy.

35. A compound or salt according to claim 34, wherein $R_1$ is hydrogen.

36. A compound according to claim 35, wherein
$R_3$ is phenyl substituted with $R_a$, $R_b$, and $R_c$, where $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl) ($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl)($C_{1-6}$ alkyl), —$CO_2$($C_{1-6}$ alkyl);
$R_4$ is selected from:
hydrogen, halogen, hydroxy, $C_{1-8}$ alkyl, —O($C_{1-8}$ alkyl), —O($C_1$–$C_6$ alkyl)N($C_1$–$C_6$ alkyl)($C_1$–$C_6$ alkyl), —$NO_2$, —CN, —$SO_2NH_2$, —$SO_2NH(C_{1-8}$ alkyl), —$SO_2N(C_{1-8}$ alkyl)($C_{1-8}$ alkyl), amino, —NH($C_{1-8}$ alkyl), —N($C_{1-8}$ alkyl)($C_{1-8}$ alkyl), —N($C_{1-8}$ alkyl)CO($C_{1-8}$ alkyl), —N($C_{1-8}$ alkyl)$CO_2$ ($C_{1-8}$ alkyl), —$NHSO_2(C_{1-8}$ alkyl), —N($C_{1-6}$ alkyl) $SO_2(C_{1-8}$ alkyl), —$SO_2NHCO(C_{1-8}$ alkyl), —$CONHSO_2(C_{1-8}$ alkyl), —CON($C_{1-8}$ alkyl)($C_{1-8}$ alkyl), —$CO_2(C_{1-8}$ alkyl), —S($C_{1-8}$ alkyl) —SO ($C_{1-8}$ alkyl), —$SO_2(C_{1-8}$ alkyl), and $Ar_2$;
$R_{10}$ is hydrogen, methyl or ethyl;
$R_{11}$ and $R_{12}$ are hydrogen; and
$R_{12}'$ is phenyl.

37. A compound according to claim 30, wherein
$R_{11}$ and $R_{12}$ are hydrogen;
$R_{12}'$ is phenyl substituted with $R_f$, $R_g$, and $R_h$, and $R_3$ is phenyl substituted with $R_a$, $R_b$, and $R_c$, where $R_f$, $R_g$, $R_h$, $R_a$, $R_b$, and $R_c$ independently represent hydrogen, halogen, hydroxy, $C_{1-6}$ alkyl, —O($C_{1-6}$ alkyl), —$NO_2$, —CN, —$SO_2NH_2$, amino, —NH($C_{1-6}$ alkyl), —N($C_{1-6}$ alkyl)($C_{1-6}$ alkyl), —N($C_{1-6}$ alkyl)CO($C_{1-6}$ alkyl), —N($C_{1-6}$ alkyl)$CO_2$($C_{1-6}$ alkyl), —CON($C_{1-6}$ alkyl) ($C_{1-6}$ alkyl), —$CO_2(C_{1-6}$ alkyl).

38. A compound according to claim 1, which is:

5-Ethyl-5-phenyl-2-(3-methoxy-2-phenylquinolin-4-yl)-imidazoline;
5-Ethyl-5-phenyl-2-(2-phenylquinolin-4-yl)-imidazoline;
5-Ethyl-5-phenyl-2-(2-phenylquinolin-4-yl)-imidazoline;
5-Ethyl-4-phenyl-2-(3-hydroxy-2-phenylquinolin-4-yl)-imidazoline;
5-Ethyl-5-phenyl-2-[3-(dimethylamino)methyl-2-phenylquinolin-4-yl]-imidazoline;
5-Isobutyl-5-phenyl-2-(3-methoxy-2-phenylquinolin-4-yl)-imidazoline;
5-Propyl-5-phenyl-2-(3-methoxy-2-phenylquinolin-4-yl)-imidazoline; or
5-Ethyl-5-phenyl-2-(6-fluoro-3-methoxy-2-phenylquinolin-4-yl)-imidazoline.

39. A compound according to claim 1, which is

2'-(3-methoxy-2-phenylquinolin-4-yl)-spiro[6,7,8,9-tetrahydro-5H-benzocycloheptene-5,4'-imidazoline]; or
2'-(3-methoxy-6-methyl-2-phenylquinolin-4-yl)-spiro[6,7,8,9-tetrahydro-5H-benzocycloheptene-5,4'-imidazoline].

40. A compound according to claim 1, which is

5-Ethyl-5-phenyl-2-[(3-(diethylamino)methyl-2-phenylquinolin-4-yl]-imidazoline;
5-Ethyl-5-phenyl-2-[3-(1-pyrrolidinyl)methyl-2-phenylquinolin-4-yl]-imidazoline;
5-Ethyl-5-phenyl-2-[3-(4-morpholinyl)methyl-2-phenylquinolin-4-yl]-imidazoline;
5-Isobutyl-5-phenyl-2-(6-fluoro-3-methoxy-2-phenylquinolin-4-yl)-imidazoline; or
5-Propyl-5-phenyl-2-(6-fluoro-3-methoxy-2-phenylquinolin-4-yl)-imidazoline.

41. A compound according to claim 10 which is 3-(3-methoxy-2-phenylquinolin-4-yl)-7a-phenyl-5,6,7,7a-tetrahydro-1H-pyrrolo[1,2-c]imidazole.

42. A compound according to claim 1, which is

5-Propyl-5-phenyl-2-(6-methyl-3-methoxy-2-phenylquinolin-4-yl)-imidazoline;
5-Propyl-5-phenyl-2-(6-chloro-3-methoxy-2-phenylquinolin-4-yl)-imidazoline;
5-Ethyl-5-phenyl-2-(6-chloro-3-methoxy-2-phenylquinolin-4-yl)-imidazoline;
5-Isopropyl-5-phenyl-2-(3-methoxy-2-phenylquinolin-4-yl)-imidazoline;
5-Ethyl-5-(3-chlorophenyl)-2-(3-methoxy-2-phenylquinolin-4-yl)-imidazoline;
5-Ethyl-5-phenyl-2-(3-butyl-2-phenylquinolin-4-yl)-imidazoline;
5-Ethyl-5-phenyl-2-(3-methoxy-6-methyl-2-phenylquinolin-4-yl)-imidazoline;
5-Ethyl-5-phenyl-2-[3-(2-hydroxyethoxy-2-phenylquinolin-4-yl]-imidazoline;
5-Ethyl-5-(4-pyridinyl)-2-(3-methoxy-2-phenylquinolin-4-yl)-imidazoline;
4-Ethyl-5-(3-pyridinyl)-2-(3-methoxy-2-phenylquinolin-4-yl)-imidazoline; or
5-Butyl-5-phenyl-2-(3-methoxy-2-phenylquinolin-4-yl)-imidazoline.

43. A compound according to claim 1, which is

5-Butyl-5-phenyl-2-(6-chloro-3-methoxy-2-phenylquinolin-4-yl)-imidazoline;
1-(2-Hydroxyethoxy)-5-ethyl-5-phenyl-2-(3-methoxy-2-phenylquinolin-4-yl)-imidazoline;
5-Ethyl-5-phenyl-2-{3-[2-(diethylamino)ethoxy]-2-phenylquinolin-4-yl}-imidazoline;
5-Ethyl-5-phenyl-2-{3-[2-(propylamino)ethoxy]-2-phenylquinolin-4-yl}-imidazoline.

5-Ethyl-5-phenyl-2-{3-[2-(dipropylamino)ethoxy]-2-phenylquinolin-4-yl}-imidazoline;

5-Ethyl-5-phenyl-2-{3-[2-(1-pyrrolidinyl)ethoxy]-2-phenylquinolin-4-yl}-imidazoline; or 1-Methyl-5-phenyl-5-ethyl-2-{3-[2-(methoxy]-2-phenylquinolin-4-yl}-imidazoline.

44. A compound according to claim 10, which is S-3-(3-methoxy-2-phenylquinolin-4-yl)-5,6,7,7a-tetrahydro-1H-pyrrolo[1,2-c]imidazole.

45. A compound according to claim 15, which is 4-Ethyl-4-phenyl-2-(2-phenylquinolin-4-yl)-imidazolin-5-one.

46. A compound according to claim 19, which is 2-(3-Methoxy-2-phenylquinolin-4-yl)-5-phenyl-5-propyl-2-oxazoline.

47. A pharmaceutical composition comprising a compound according to claim 1 combined with at least one pharmaceutically acceptable carrier or excipient.

48. A pharmaceutical composition comprising a compound according to claim 15 combined with at least one pharmaceutically acceptable carrier or excipient.

49. A pharmaceutical composition comprising a compound according to claim 19 combined with at least one pharmaceutically acceptable carrier or excipient.

50. A pharmaceutical composition comprising a compound according to claim 24 combined with at least one pharmaceutically acceptable carrier or excipient.

51. A pharmaceutical composition comprising a compound according to claim 30 combined with at least one pharmaceutically acceptable carrier or excipient.

52. A compound which is selected from 5-phenyl-2-(3-methoxy-2-phenylquinolin-4-yl)-imidazoline;

5-Methyl-5-phenyl-2-(3-methoxy-2-phenylquinolin-4-yl)-imidazoline; and the pharmaceutically acceptable salts thereof.

* * * * *